US005693781A

United States Patent [19]

Zupancic et al.

[11] Patent Number: 5,693,781
[45] Date of Patent: Dec. 2, 1997

[54] PROMOTER DNA FRAGMENT FROM CORYNEFORM BACTERIA

[75] Inventors: Thomas J. Zupancic, Worthington, Ohio; Hideaki Yukawa, Inashiki-gun, Japan

[73] Assignee: Mitsubishi Chemical Corporation, Tokyo, Japan

[21] Appl. No.: 76,091

[22] Filed: Jun. 15, 1993

Related U.S. Application Data

[63] Continuation-in-part of Ser. No. 709,151, Jun. 3, 1991, abandoned.

[51] Int. Cl.$^6$ .......................... C07H 21/04; C12W 15/63
[52] U.S. Cl. .................. 536/24.1; 435/172.3; 435/320.1
[58] Field of Search .................... 435/91.1, 91.21, 435/172.1, 172.3, 320.1, 840, 843; 536/23.1, 24.1

[56] References Cited

FOREIGN PATENT DOCUMENTS

| 0530765 | 3/1993 | European Pat. Off. . |
| 3147792 | 6/1991 | Japan . |
| 5015378 | 1/1993 | Japan . |
| WO8809819 | 12/1988 | WIPO . |

OTHER PUBLICATIONS

Santamaria et al. (1987) Gene, vol. 56, pp. 199–208.
Bardonnet et al. (1991) FEMS Microbiology Letters, vol. 84, pp. 97–102.
Takagi et al. (1986) Agricultural & Biological Chemistry, vol. 50, pp. 2597–2603.
Eikmanns et al, A family of *Corynebacterium glutamicum/Escherichia coli* shuttle vectors for cloning, controlled gene expression, and promotor brobing, *Gene* 102 (1991) pp. 93–98.
Barak et al, Construction of a promoter–probe shuttle for *Escherichia coli* and *Brevibacteria*, *Gene*, 95 (1990), pp. 133–135.

*Primary Examiner*—Nancy Degen
*Attorney, Agent, or Firm*—Sughrue, Mion, Zinn, Macpeak & Seas, PLLC

[57] ABSTRACT

Coryneform bacteria promoter DNA fragments are disclosed having greater promoter strength in Coryneform bacteria cells than the tac promoter obtained by fusing *Escherichia coli* trp promoter and lac promoter. The promoter function of some of the promoter DNA fragments is controllable by replacing at least one of the culture-medium ingredients with at least one other ingredient. The sizes and nucleotide sequences of such promoter DNA fragments are also disclosed.

3 Claims, 6 Drawing Sheets

PROMOTER DNA FRAGMENT FROM
CORYNEFORM BACTERIA

CROSS REFERENCE TO RELATED APPLICATIONS

The present application is a continuation in part of U.S. application Ser. No. 07/709,151, filed Jun. 3, 1991, now abandoned, the disclosure of which is hereby incorporated by reference.

FIELD OF THE INVENTION

The present invention relates to a promoter DNA fragment originating from chromosomal DNA of a coryneform bacterium.

BACKGROUND OF THE INVENTION

Coryneform bacteria are Gram-positive bacteria widely used for industrial-scale production of a variety of products including amino acids, such as glutamic acid and aspartic acid; and purine nucleotides, such as inosinic acid, etc. However, compared with *Escherichia coli*, coryneform bacteria have not been extensively bred by using recombinant DNA techniques. To fully utilize the recombinant DNA techniques for breeding of coryneform bacteria, a vector must be developed useful for industrial-scale gene manipulation in coryneform bacteria. More particularly, a promoter DNA fragment of such a vector must be developed, i.e., a promoter having a strong gene-expression function or a promoter whose gene-expression function is controllable.

Improvement of promoter function in coryneform bacteria has been reported by using promoters originating from *Escherichia coli*. The Journal of Biotechnology, 5, 305, (1987) and Gene, 102, 93, (1991) state that a tac promoter (Gene, 20, 231 (1982)) obtained by fusing a protein of trp promoter and lac promoter both originating from *Escherichia coli* achieved a greater constitutive promoter strength in coryneform bacteria than any other promoter examined so far.

As far as the inventors know, no promoter has since been developed that achieves a greater promoter strength in coryneform bacteria than the tac promoter.

A method for controlling the expression of a gene of interest in a coryneform bacterium is described in Bio/Technology, 6, 428, (1988), in which a controllable promoter originating from *Escherichia coli* is incorporated into a coryneform bacterium without modifying the promoter. However, this gene-expression control method fails to achieve a level of expression of a gene of interest in the host coryneform bacterium comparable to the level that is achieved by the same promoter in *Escherichia coli*.

In developing a system for manipulating the expression of cloned genes in coryneform bacteria for which no such system exists, it is desirable to begin by isolating a variety of different promoter elements with different functional properties. Functional properties of interest may indicate whether a promoter is one which is repressed under some conditions, but induced under other culture conditions. Use of controllable promoters allows the expression of cloned genes to be induced or repressed in a controlled manner.

SUMMARY OF THE INVENTION

Accordingly, an object of the present invention is to obtain a promoter DNA fragment which shows the expression of a gene of interest in coryneform bacteria at a high rate. More particularly, an object of the present invention is to obtain from the chromosome of a coryneform bacterium a promoter DNA fragment having greater promoter strength than the above-described *E. coli* tac promoter, and to obtain from the chromosome of a coryneform bacterium a promoter DNA fragment which is useful for controlling the expression of a gene of interest in a coryneform bacterium.

The inventors of the present invention have found that such a promoter DNA fragment can be obtained from coryneform bacteria by using a novel promoter probe shuttle vector constructed by the inventors. The promoter probe shuttle vector comprises:

a) a replication origin DNA region that is functional in *Escherichia coli*, b) a replication origin DNA region that is functional in coryneform bacteria, c) a DNA region including a selectable marker gene, d) a DNA region including a reporter gene, the DNA region including a gene which lacks its own promoter region and differs from the selectable marker gene of C) in phenotype, and e) a transcription terminator located in the upstream from the DNA region d) including the reporter gene.

Based on the above finding, the invention provides:

(1) a promoter DNA fragment which is obtained from a chromosome of a coryneform bacterium and is functional in coryneform bacteria, the promoter DNA fragment having a greater promoter strength in coryneform bacteria than the tac promoter, and (2) a controllable promoter DNA fragment which is obtained from a chromosome of a coryneform bacterium and is functional in coryneform bacteria, wherein the promoter function of the controllable promoter DNA fragment is controllable by replacing at least one substance which is contained in the culture medium for the host coryneform bacterium and is assimilable by the host coryneform bacterium, with at least one other substance which is assimilable by that the host coryneform bacterium.

DESCRIPTION OF THE PREFERRED EMBODIMENTS

Figure 1:
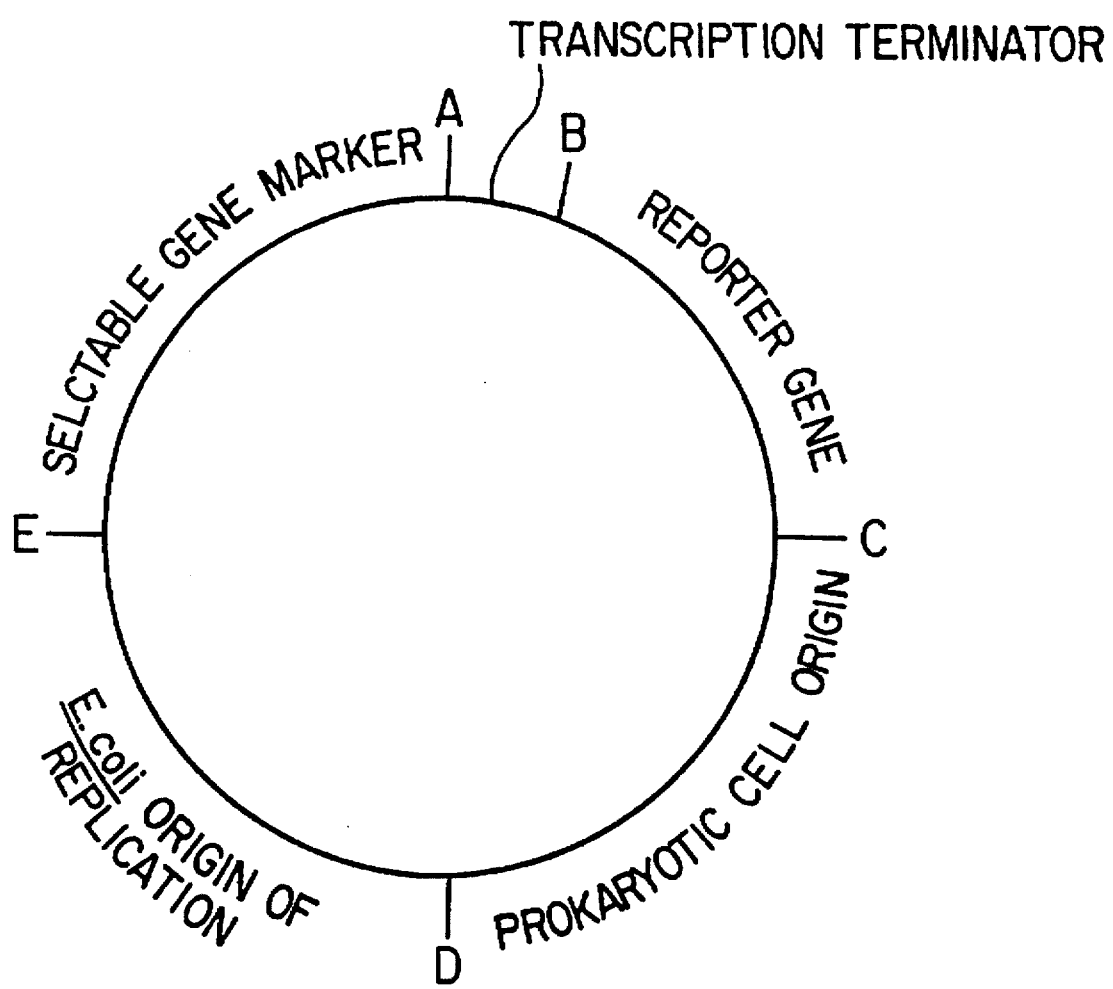
FIG. 1 shows the promoter probe shuttle vector useful for detecting a promoter DNA fragment in coryneform bacteria according to the present invention.

The present invention will be described in detail hereinafter.

First, several terms used in this specification will be defined. The term "promoter" means a DNA region to which an RNA polymerase specifically binds so as to initiate the transcription of the gene. The term "tac promoter" means a promoter obtained by fusing a sequence obtained from −35 region of a tryptophan operon promoter of *Escherichia coli* and a sequence obtained from −10 region of a lactose operon promoter of *Escherichia coli*. The term "promoter DNA fragment" means a synthetic DNA fragment or a DNA fragment obtained from a naturally occurring chromosome DNA, either of which has the function to initiate the transcription of a gene, that is, a gene transcription function, and includes a promoter as defined above. The term "promoter DNA fragment having a greater promoter strength than a tac promoter" means an above-defined promoter DNA fragment which has a stronger gene-transcription initiating capability than the tac promoter. The term "controllable promoter DNA fragment" means a promoter DNA fragment whose function to initiate the transcription of a gene can be controlled, that is, can be induced when the function has been repressed, or repressed when the function has been induced, by replacing at least one substance that is contained in the culture medium for a host coryneform bacterium having the promoter DNA fragment and useful for the host bacterium, with at least one other substance. The term "coryneform bacteria" means a group of microorganisms defined in Bargeys Manual of Determinative Bacteriology, 8, 599, (1974), that is, rod-shaped bacteria which are aerobic, Gram positive, non-acid-fast and non-sporogenous. According to the present invention, particularly preferred coryneform bacteria as the gene sources or host microorganisms of promoter DNA are the following coryneform bacteria:

*Brevibacterium ammoniagenes* ATCC 6871
*Brevibacterium divaricatum* ATCC 14020
*Brevibacterium saccharolyticum* ATCC 14066
*Brevibacterium immariophilium* ATCC 14068
*Brevibacterium lactofermentum* ATCC 13869
*Brevibacterium roseum* ATCC 13825
*Brevibacterium linens* ATCC 9174
*Brevibacterium flavum* ATCC 13826
*Brevibacterium flavum* MJ-233 (FERM BP-1497)
*Brevibacterium stationis* IFO 12144 (FERM BP-2515)
*Brevibacterium thiogenitalis* ATCC 19240
*Corynebacterium acetoacidophilum* ATCC 13870
*Corynebacterium acetoglutamicum* ATCC 15806
*Corynebacterium callunae* ATCC 15991
*Corynebacterium glutamicum* ATCC 13032, ATCC 13060
*Corynebacterium lilium* ATCC 15990
*Corynebacterium melassecola* ATCC 17965

*Brevibacterium flavum* MJ-233 and *Brevibacterium stationis* IFO 12144 listed above have been deposited under deposit Nos. FERM BP-1497 and FERM BP-2515, respectively, at Fermentation Research Institute, Agency of Industrial Science and Technology (now National Institute of Bioscience and Human- Technology), 1-3, Higashi 1-chome, Tsukuba-shi, Ibaragi-ken 305, Japan, under the Budapest Treaty. The other coryneform bacteria having ATCC numbers are described in American Type Culture Collection, Catalogue of Bacteria and Phages. All the above-listed bacteria are publicly available.

These coryneform bacteria can be incubated in known culture media widely used for coryneform bacteria, and can be recovered from the cultures.

A promoter DNA fragment according to the present invention can be obtained from naturally occurring chromosomes of micro-organisms, though such a promoter DNA fragment may be synthesized after its nucleotide sequence has been determined. *Brevibacterium flavum* MJ-233 (FERM BP-1497) is preferred as a source microorganism for the promoter DNA fragment.

To isolate a promoter DNA fragment from any of the above coryneform bacteria, chromosome DNA is extracted from the bacterium by, for example, a method described in Biochimica et Biophysica Acta., 72, 619, (1963), and then digested into relatively short DNA fragments by using suitable restriction enzymes, preferably, one or more restriction enzymes which recognize 4-base sequences, for example, AluI, HaeIII, AccII or AfaI.

A promoter DNA fragment can be isolated from the restriction fragments of the chromosome DNA by using promoter probe shuttle vectors.

Promoter Probe Shuttle Vector

A preferred promoter probe shuttle vector is the novel vector constructed by the inventors, the vector comprising:

a) a replication origin DNA region functional in *Escherichia coli*, b) a replication origin DNA region functional in coryneform bacteria, c) a DNA region including a selectable marker gene, d) a DNA region including a reporter gene, and e) a transcription terminator located in the upstream from the DNA region d) including a reporter gene.

The DNA region functional in *Escherichia coli* a) (hereinafter, referred to as "region a") is not particularly restricted as long as it controls self-replication of the plasmid in *Escherichia coli*. Region a may be attained by using a DNA fragment obtained from, for example, the plasmid pACYC184 (a product of Nippon Gene Co., Ltd.), the plasmid pBR322 (a product of TAKARA SHUZO Co. Ltd.).

The DNA region functional in coryneform bacteria b) (hereinafter, referred to as "region b") is not particularly restricted as long as it controls self-replication of the plasmid in coryneform bacteria. Region b may be obtained by using, for example, the plasmid pCRY3 (a plasmid possessed by *Brevibacterium flavum* MJ-233 GE102, described in U.S. Pat. No. 5,185,262), the plasmid pCRY2 (a plasmid possessed by *Brevi-bacterium flavum* MJ-233 GE101, described in U.S. Pat. No. 5,185,262), the plasmid pAN330 (described in Japanese Patent Application Laid-open No. 58-67679 (1983)), or the plasmid pHM1519 (described in Japanese Patent Application Laid-open No. 58-77895 (1983) ).

The above-mentioned *Brevibacterium flavum* MJ-233 GE101 and *Brevibacterium flavum* MJ-233 GE102 have been deposited under deposit Nos. FERM BP-2512 and FERM BP-2513, respectively, at Fermentation Research Institute, Agency of Industrial Science and Technology, under the Budapest Treaty.

The DNA region c) including a selectable marker gene (hereinafter, referred to as "region c" or "the marker gene") is not particularly restricted as long as it can be used as a marker of the plasmid and includes a gene different in phenotype from the gene present in the DNA region d) including a reporter gene. Region c may be obtained by, for example: a 1,300 bp DNA fragment which is obtained by digesting, with restriction enzyme BamHI, the plasmid pJCM1 that has been constructed by inserting approximately −3.0 Kb BamHI-PvuII fragment of Transposon 9 (Nature, 293, 309–311 (1981)) including a chloramphenicol resistance gene into BamHI and PvuII sites of the plasmid pBR322 and which includes a chloramphenicol resistance gene; a 787 bp DNA fragment which is obtained by digesting the plasmid pCM7 (a product of Pharmacia Co., Ltd.) with restriction enzyme HindIII and includes a Chloramphenicol resistance gene; Chloramphenicol Acetyltransferase GenBlock having a size of 792 bp (a product of Pharmacia Co., Ltd.); or a 1,426 bp DNA fragment which is obtained by digesting the plasmid pBR322 (a product of Takara Shuzo Co., Ltd.) with restriction enzymes EcoRI and AvaI and includes a tetracycline resistance gene.

The DNA region d) including a reporter gene hereinafter, referred to as "region d" or "the reporter gene") is not particularly restricted as long as it can be used as a marker of the plasmid and includes a gene which lacks its own promoter and differs from the marker gene present in region c. Region d may be constituted by, for example: an approximately −1.6 Kb DNA fragment which includes a kanamycin resistance gene and is obtained by digesting, with restriction enzymes BglII and BamHI, the plasmid pKPG13 that has been constructed by inserting an approximately −5.9 Kb BamHI-SalI fragment of Transposon 5 (described in Molecular and General Genetics, 177, 65 (1979)) including NPTII (a kanamycin resistance gene) into BamHI and SalI sites of the plasmid pBR322; a 1,494 bp DNA fragment which is obtained by digesting the plasmid pNEO (a product of Pharmacia Co., Ltd.) with restriction enzymes HindIII and BamHI and includes a kanamycin resistance gene; Kanamycin Resistance GenBlock having a size of 1,282 bp (a product of Pharmacia Co., Ltd.); or a 3,117 bp or approximately −3.3 Kb DNA fragment which is obtained by digesting the plasmid pMC1871 (a product of Pharmacia Co., Ltd.) or pSGMU32 (a product of Pharmacia Co., Ltd.) with restriction enzyme BamHI or restriction enzymes SacI and SalI, respectively, and which includes a β-galactosidase gene.

The transcription terminator e) located in the upstream from the reporter gene (region d) (hereinafter, referred to as "region e" or "the transcription terminator") may be a trpA terminator of a tryptophan operon of *Escherichia coli* which includes the following nucleotide sequence (SEQ ID NO: 18):

5'AATTCTCGCGATAATTAATTAATAGC-
CCGCCTAATGAGCGGGCTTTTTTTTTGATATCAATT3'

3'TTAAGAGCGCTATTAATTAAT-
TATCGGGCGGATTACTCGC-
CCGAAAAAAAACTATAGTTAA5'

Such a trpA terminator may be chemically synthesized by a DNA synthesizer.

Next described will be a method for constructing a promoter probe shuttle vector comprising the above-described five DNA regions a to e, which vector is used to obtain a promoter DNA fragment according to the present invention.

First, region a and region c including a selectable marker gene (this marker gene will be used as a marker in the process of constructing a promoter probe shuttle vector) are ligated with a DNA ligase to construct a plasmid which includes a marker gene and is capable of replication in *Escherichia coli*. Then, the plasmid having regions a and c is cleaved with a suitable restriction enzyme, followed by coupling the transcription terminator (region e) to one of the ends thereof and then ligating the reporter gene (region d) to the downstream end of the transcription terminator. Finally, the thus-obtained plasmid which includes the transcription terminator (region e), the reporter gene (region d) located in the downstream end of the transcription terminator and the marker gene (region c), and which is capable of replication in *Escherichia coli* is cleaved with a suitable restriction enzyme, followed by ligating region b to the cleavage with a DNA ligase. A promoter probe shuttle vector is thus constructed.

Examples of the promoter probe shuttle vector thus constructed are:

a plasmid pPROBE17 consisting essentially of a) a plasmid replication origin region that is functional in *Escherichia coli* (a DNA fragment obtained by coupling a promoter to a 1.1 Kb DNA fragment obtained by digesting the plasmid pBR322 with restriction enzymes BstY1 and PvuII), b) a plasmid replication origin region that is functional in coryneform bacteria (a 4.0 Kb DNA fragment obtained by digesting the plasmid pCRY3 with restriction enzyme XhoI), c) a chloramphenicol resistance gene (a 1.3 Kb DNA fragment obtained by digesting the plasmid pJCM1 with restriction enzyme BamHI), d) a kanamycin resistance gene lacking its own promoter (a 3.3 Kb DNA fragment obtained by digesting the plasmid pKPG13 with restriction enzymes BglII and BamHI), and e) a transcription terminator (a trpA terminator, that is, the above-described 61 bp synthetic DNA fragment) located in the upstream from the kanamycin resistance gene; and a plasmid p13Bgal consisting essentially of a) a plasmid replication origin region that is functional in *Escherichia coli* (a DNA fragment the same as in the above-described plasmid pPROBE17), b) a plasmid replication origin region that is functional in coryneform bacteria (a DNA fragment the same as in the above-described plasmid pPROBE17), c) a chloramphenicol resistance gene (a DNA fragment the same as in the above-described plasmid pPROBE17), d) a β-galactosidase gene lacking its own promoter (a 3.3 Kb DNA fragment obtained by digesting the plasmid pSGMU22 with restriction enzymes SacI and SalI), and e) a transcription terminator (a DNA fragment the same as in the above-described plasmid pPROBE17) located in the upstream from the kanamycin resistance gene.

The construction of the plasmid pPROBE17 shown in FIGS. 2 and 3 will be described in detail in Example 1. The restriction map of the plasmid p17Bgal is shown in FIG. 4.

Set forth below is a description of a method for isolating a promoter DNA fragment according to the present invention from chromosomal DNA of coryneform bacteria cells by using promoter probe shuttle vectors as described above.

Promoter DNA Fragment Isolation Method

Promoter probe shuttle vectors as described above are introduced into coryneform bacteria cells by a known transformation method, for example, the electroporation method (Agricultural and Biological Chemistry, 54, 443, (1990)). The transformants are cultured in a suitable medium to confirm that the reporter gene (region d) is not expressed (the gene remains unexpressed because the reporter gene lacks its own promoter). If the reporter gene is an antibiotic resistance gene, whether the reporter gene is expressed and how strongly it is expressed can be easily determined by plating the transformants on selection media containing the antibiotic concerned and examining the antibiotic sensitivity of the transformants. Determination of the expression of the reporter gene and the strength of its expression can also be performed by culturing the transformants in ordinary media and investigating the cultures for the expression product of the reporter gene on the basis of characteristics or properties of the product. For example, if the reporter gene is a β-galactosidase gene, the transformants are plated on selection media containing 5-bromo-4-chloro-3-indolyl-β-D- galactoside (X-gal), that is, a substrate of β-galactosidase, and measuring the color tone of the colonies of transformants, that is, colonies which exhibit blue color as a result of decomposition of the X-gal by the action of β-galactosidase expressed.

The promoter probe shuttle vectors whose reporter gene expression has been confirmed to be inactive in the coryneform bacterium are cleaved by a suitable restriction enzyme which recognizes a unique site between the reporter gene (region d) and the transcription terminator (region e). The resultant DNA fragments are ligated with a DNA ligase to DNA fragments obtained by digesting chromosome DNA of the coryneform bacterium with a 4-base-sequence-recognizing restriction enzyme. The thus-constructed plasmids are introduced into coryneform bacteria cells by the electroporation method or the like.

The thus-obtained transformants are cultured, and the reporter gene expression is examined by a method described above. The transformants whose reporter gene expression has been confirmed to be active are recovered, thus obtaining coryneform bacteria cells which have been transformed with promoter probe shuttle vectors containing promoter DNA fragments. A promoter DNA fragment according to the present invention can be obtained from these coryneform bacteria cells capable of the expression of reporter gene by a method described below.

Promoter DNA Fragment of the Invention Having Greater Promoter Strength Than the tac Promoter First, a method will be described for obtaining a promoter DNA fragment of the invention having a greater promoter strength than the tac promoter.

The tac promoter, serving as a standard for promoter strength comparison, is inserted into a promoter probe shuttle vector at a site between the reporter gene (region d) and the transcription terminator (region e) by the above-described method. The resultant plasmid is introduced into coryneform bacteria cells by the electroporation method, followed by examining the reporter gene expression strength by a method as described above. The tac promoter used in this process may be, for example, a 96 bp DNA fragment obtained by digesting the plasmid pDR540 (Pharmacia Co., Ltd.) with restriction enzymes HindIII and BamHI, or a DNA fragment accordingly synthesized by a DNA synthesizer.

With reference to the reporter gene expression strength in the coryneform bacteria cells transformed with the above-described promoter probe shuttle vector containing the tac promoter, the reporter gene expression strengths of coryneform bacteria cells transformed with promoter probe shuttle vectors containing DNA fragments obtained from chromosomal DNA of the coryneform bacterium are examined, and the cells exhibiting greater expression strength are selected. Thus, transformants containing promoters having greater promoter strength than the tac promoter are obtained.

To determine whether the enhancement in the reporter gene expression in each of the transformants is caused by the promoter contained in the promoter probe shuttle vector or a mutation in the chromosome of the host cell, plasmid DNA is extracted from each transformant and introduced again into coryneform bacteria cells, followed by an examination of the reporter gene expression strength of the transformed cells. The transformants whose reporter gene expression enhancement has been confirmed to be caused by the promoter are recovered.

Examples of the transformants thus obtained are: the below-listed twelve strains of Brevibacterium flavum MJ-233 which have been transformed with plasmids obtained by inserting AluI-HaeIII restriction fragments of chromosome DNA of Brevibacterium flavum MJ-233 (FERM BP-1497) into the above-described promotor probe shuttle vectors pPROBE17 at the restriction enzyme EcoRV recognition site, and which are resistant to kanamycin concentration of 500 µg/ml or greater, that is, able to grow on a medium containing 500 µg/ml or more of kanamycin. These twelve transformants and the plasmids contained therein are named as follows:

| No. | Bacteria strain | Plasmid |
|---|---|---|
| (1) | Brevibacterium flavum MJ-233 Km5001 | pPROBE17 Km5001 |
| (2) | Brevibacterium flavum MJ-233 Km5002 | pPROBE17 Km5002 |
| (3) | Brevibacterium flavum MJ-233 Km5003 | pPROBE17 Km5003 |
| (4) | Brevibacterium flavum MJ-233 Km5004 | pPROBE17 Km5004 |
| (5) | Brevibacterium flavum MJ-233 Km5005 | pPROBE17 Km5005 |
| (6) | Brevibacterium flavum MJ-233 Km5006 | pPROBE17 Km5006 |
| (7) | Brevibacterium flavum MJ-233 Km5007 | pPROBE17 Km5007 |
| (8) | Brevibacterium flavum MJ-233 Km5008 | pPROBE17 Km5008 |
| (9) | Brevibacterium flavum MJ-233 Km5009 | pPROBE17 Km5009 |
| (10) | Brevibacterium flavum MJ-233 Km5010 | pPROBE17 Km5010 |
| (11) | Brevibacterium flavum MJ-233 Km5011 | pPROBE17 Km5011 |
| (12) | Brevibacterium flavum MJ-233 Km5012 | pPROBE17 Km5012 |

The kanamycin resistances of the transformants are summarized in Table 1. Brevibacterium flavum MJ-233 transformed with a plasmid obtained by inserting the tac promoter to the promoter probe shuttle vector pPROBE17 at the EcoRV site was not resistant to even 500 µg/ml of kanamycin, that is, was not able to grown on a medium containing 500 µg/ml of kanamycin.

TABLE 1

| Kanamycin concentration in medium (µg/ml) | 500 | 750 | 1000 | 1500 |
|---|---|---|---|---|
| Nos. of transformants | 5 | 4 | 1 | 2 |

Determination of the Size of Nucleotide Sequence of Promoter DNA Fragment of the Invention Having Greater Promoter Strength Than tac Promoter A promoter DNA fragment according to the present invention having greater promoter strength than the tac promoter is obtained from a transformant isolated as described above. The size and nucleotide sequence of such a promoter DNA fragment can be determined as follows.

First, primer DNA fragments are chemically synthesized corresponding to nucleotide sequences of a plasmid probe shuttle vector present in the upstream and downstream from a restriction enzyme recognition site (a restriction enzyme recognition site between regions d and e) at which a fragment from chromosomal DNA of a coryneform bacterium is inserted. If the promoter probe shuttle vector is the plasmid pPROBE17, the following primer DNA fragments are chemically synthesized corresponding to nucleotide sequences of the plasmid in the 5' and 3'-flanking regions of the EcoRV site.

| | | |
|---|---|---|
| GATCAGATCCCAGAATTGAT | (Primer DNA for the 5' end) | (SEQ ID No. 19) |
| TGAGCGGGCTTTTTTTTGAT | (Primer DNA for the 3' end) | (SEQ ID No. 20) |

Using the above primer DNA sequences, plasmid DNA extracted from transformants isolated as described above is locally amplified by the PCR method (Nature, 324, 163 (1986)) using a DNA Thermal Cycler model 480 (Takara Shuzo Co., Ltd.). Thus, a portion substantially consisting of the insert DNA fragment into the plasmid can be selectively replicated many times (i.e., amplified).

The insert DNA fragment thus amplified is electrophoresed on an agarose gel followed by determining the size thereof based on the migration distance thereof on the agarose-gel with reference to the migration distance-size standard curve obtained by the electrophoresis of DNA fragments of known sizes (for example, pHY markers by Takara Shuzo Co., Ltd.) on the same agarose gel.

The nucleotide sequence of the amplified insert DNA fragment can be determined by the dideoxy chain termination method (Proceedings of the National Academy Science of the United States of America, 74, 5463 (1977)) using the same primers as used in the PCR method and the products of the PCR method as templates.

The sizes and nucleotide sequences of the insert DNA fragments contained in the above-listed promoter probe shuttle vectors of the twelve transformants were determined as follows:

| No. | Plasmid | Size of insert DNA fragment | Sequence of insert DNA fragment |
|---|---|---|---|
| (1) | pPROBE17 Km5001 | about 130 bp | SEQ ID No: 1 |
| (2) | pPROBE17 Km5002 | about 410 bp | SEQ ID No: 2 |
| (3) | pPROBE17 Km5003 | about 420 bp | SEQ ID No: 3 |
| (4) | pPROBE17 Km5004 | about 240 bp | SEQ ID No: 4 |
| (5) | pPROBE17 Km5005 | about 600 bp | SEQ ID No: 5 |
| (6) | pPROBE17 Km5006 | about 590 bp | SEQ ID No: 6 |
| (7) | pPROBE17 Km5007 | about 430 bp | SEQ ID No: 7 |
| (8) | pPROBE17 Km5008 | about 860 bp | SEQ ID No: 8 |
| (9) | pPROBE17 Km5009 | about 1190 bp | SEQ ID No: 9 |
| (10) | pPROBE17 Km5010 | about 710 bp | SEQ ID No: 10 |
| (11) | pPROBE17 Km5011 | about 1000 bp | SEQ ID No: 11 |
| (12) | pOROBE17 Km5012 | about 740 bp | SEQ ID No: 12 |

SEQ ID NO. 1:

```
GATCCATGCA  CGCGCGTTGC  TCGGGCTGAA  GGCCTGCTTC  CACCTCAGCG  GTGTGTTCAC   60
GGCGATCAAT  TTCTTTACCA  CCGAACACAT  ATCCATCACT  GGCCCATACT  CACCCCGACC  120
TGTAGGAT                                                                128
```
SEQ ID NO. 2:

```
GATCCACGCT  GAGCATTTGA  AAGTAACTAG  TCCCGAAGAT  CTTCGGAAAT  GCATAAAGCA   60
AAAGGCTCTT  AGTGGTTTGT  CAGCGTATGA  TCATCACGTA  GAGTAACACC  CAAGAGTAAG  120
ACGCAACATC  AATCAATGTG  CAAGGGTTTC  ATTTCTGGAA  ATCGTGGTCA  CCCCACATTC  180
ACCAGTAATG  AACAAGCTTG  TTTAATGTGA  ATTTGGAGTA  GACCACATGC  CCACTCTCGG  240
ACCATGGGAA  ATTGGAATCA  TTGTCCTGCT  GATCATCGTG  CTGTTCGGCG  CGAAGAAGCT  300
GCCTGATGCA  GCTCGTTCCA  TCGGCCAGAT  AACCCGCAGA  TCAAGACATC  AAACATTCGC  360
ACCATCGGAT  TTCTCATCTA  CGACGGCGTC  TCACCCCTCG  ATTTCACTGG  ATC         413
```
SEQ ID NO. 3:

```
GATCCCTGCC  CAGGCGCGCG  CCCGTCCTGG  CGAGTTCGCA  GATCGAAGGG  TTTGAACACC   60
GTAGAGGGTG  GCGTCGACAA  GCAAATTTCT  GGTTTGCTGC  AAGCCTTGCC  CTGTACTGGT  120
GCGCCGCGCT  GTGGATCGCG  CTGGACGTTG  GGTATTTCTG  GGGCGACGCG  CTCTCGCGCA  180
CCCAAGGCGC  CCTATCCGCG  CTGTACTCGC  GCAACCCCAC  GTTGTCGGCG  ATCGGTTACG  240
TGTTTACCCC  TCTGACCACC  GTGGTGCAGA  TTCCATTGGT  GGCGCTGAGC  CCCTGGGTCC  300
CGGAATTCAC  GCGCGCCGGG  TTGGCAGGCG  CATTGGTGTC  ATCAGTGTTC  ATGGCGGCTT  360
CAGTGAGGCA  ATTGTGGTTG  ATTGCCAGCG  AGCGCAACAT  CCGGTATTGG  CTCGCGGTGG  420
TAG                                                                    423
```
SEQ ID NO. 4:

```
GATCTTTCAG  CTGCTCACAC  GTGATTGTAC  CGCGTCAATG  GAAGTGATTG  GCCGCTTCCT   60
TGCCTTGCTG  GAATTGTATA  AGGCACGCGC  TATTGAAACC  TTGCAAGAGG  AGCCACTCGG  120
CGAGCTTAAA  GTTTCGTGGA  CTGGCATTGA  TGTCGATCCA  GCAGTCGTCG  CGGCGAGTGA  180
CTGGGAGTAA  TCAGTTTTTC  TTAAGGAAAC  GTTGCTGAAT  TAGTTTTAGT  GACCTAAGAT  240
C                                                                      241
```
SEQ ID NO. 5:

```
GATCTTGTCG  ACGCCGCCCG  CGACAGTGGC  GCACAAATCC  TCACGGGCGG  CCAACCCTCA   60
GATGGACCTG  GAAACTTCTA  TCCGGCCACG  ATTGTTACAG  ACATTGCTCC  GGATAATCCT  120
CTGGTTGTTG  AAGAACAGTT  CGGACCAGCG  CTTCCAATAG  TCCGATACTC  CAATATTGAT  180
GAAGCCATTG  GTTGGGCAAA  TGGACTTGAA  GTAGGTCTTG  GAGCTTCTGT  GTGGTCCGCT  240
GATCGGAATC  GCGCAATGGA  TGTAGCTAGG  CAGATTCAGG  CTGGAACAGT  ATGGATTAAT  300
AACCATGCCC  GCCCTGATCC  AAGAATTCCT  TTCGGCGGAA  TCAAGCAATC  GGGATACGGC  360
CTTGAATTTG  GTGCTGATGG  CCTCAAAGCG  GTTGCGGTCC  CCAAGGTCTA  CAACGGTTAA  420
TTGTTTGATG  TTGAGAATTC  TCCGGGCCGA  TTATTGTCGT  AGTTTTCTGC  ATTGGTGCTT  480
```

-continued

| | | | | | | |
|---|---|---|---|---|---|---|
| GGCAAGGAGA | TCTGCCCCTG | GTAAAGCTTG | ATCAAATCGC | ATTTGACCAG | GGGATTTGGT | 540 |
| GTATTGTTAA | CTTGAAGGTA | GAGTATATTC | TCGTTCCTAA | AGGGGCCTAT | AGATC | 595 |

SEQ ID NO. 6:

| | | | | | | |
|---|---|---|---|---|---|---|
| GATCTGAAGC | AACACCTGAT | CAACCACACC | CCTTGGGGCG | CAAAGATCAC | GGTGGAGATC | 60 |
| GATGACATTA | ACCAACCGTT | CTCCACCGAT | ATTACCGGCC | CTGCAATGTC | CACCCTGGCG | 120 |
| TCCTGCCTGA | GCGCTGCGTA | CGAGGGCAAG | GATCTTGTCA | CCGAAGGCAG | CGGCGGATCC | 180 |
| ATTCCACTGT | GCACCGAACT | GATTGAGGTC | AACCCAGAAG | CAGAATTGGC | ACTCTACGGT | 240 |
| GTGGAAGAAC | CCCTCACCGT | TATCCACTCC | GCTAATGAAT | CTGTTGACCC | CAATGAGATT | 300 |
| CGCGATATCG | CCACCGCAGA | AGCATTGTTC | CTGCTCAACT | ACACCAAGTA | GACTTAGAAG | 360 |
| CAGGCATTAA | CACTGCCACC | TTTGCAAAAT | TAACCACCCC | CTGATGGGGT | GGTTTTTTCA | 420 |
| TGAGTTGAAA | AAAGTGTCTT | GATTCACTTT | GTGATGACGG | TTACCATAGC | CATCGTGACT | 480 |
| AAAAACATTG | ACCTTAAGCG | AGTAGCCAAG | GCTACGTACC | CTACTGCGGG | ATAGATGGAC | 540 |
| TGGCTCCCCG | CACTAGGGAA | GTAGTCGTTA | ATCAACACCA | AGAAGATC | | 588 |

SEQ ID NO. 7:

| | | | | | | |
|---|---|---|---|---|---|---|
| GATCTCAACG | TTTAGCGGCT | CTCTGGATCG | TGAAATGTCA | ACGTTCATGG | AAGCCAATGT | 60 |
| AGTGGGGTCG | CGTCGAAAAG | CGCGCTTTAA | GGGCGACACG | CCCAAAAAGT | TTTACCTTTA | 120 |
| AAAACTACCC | GCACGCAGCA | CGAACCTGTT | CAGTGATGCA | AATCACCGCT | AAAATATTGT | 180 |
| GGACGTTACC | CCCGCCTACC | GCTACGATTT | CAAAACATGA | CCATTTCCTC | ACCTTTGATT | 240 |
| GACGTCGCCA | ACCTTCCAGA | CATCAACACC | ACTGCCGGCA | AGATCGCCGA | CTTTAAGGCT | 300 |
| CGCCGCGCGG | AAGCCCATTT | CCCCATGGGT | GAAAAGGCAG | TAGAGAAGGT | CCACGCTGCT | 360 |
| GGACGCCTCA | CTGCCCGTGA | GCGCTTGGAT | TACTTACTCG | ATGAGGGCTC | CTTCATCGAG | 420 |
| ACCGATCAGA | TC | | | | | 432 |

SEQ ID NO. 8:

| | | | | | | |
|---|---|---|---|---|---|---|
| CCGTTATATA | TAAGGAATAG | GCAACAAGTC | CCACTGGCTG | TGCCAATAGC | CAGCACACAA | 60 |
| ACATTGAATC | CCCACAGATC | ATCACCCAAA | ACTACGGGGC | TTGCAGTTCC | AATGCGATCA | 120 |
| AACCCATGGA | CAACATTGCC | ATGCGGATGC | TTCAGTTTTG | AATGAGGAGA | GCGGTAGATT | 180 |
| AGCCAACCGT | CAATTAATGA | CAATTGCCAC | CACAACAGCT | AACGCGAAGA | AGAAATCTGC | 240 |
| GACGACTGGA | AAACATGGA | TTTTCAACAG | TGATGACAAC | AATGAGATGC | CCATGAGGGA | 300 |
| ACCAGCCCAC | GAGGGGCCCC | TTTGTGACAT | CGGCGTAGTT | GTTCAACTAT | AATGGAACGC | 360 |
| TGATCGTGGA | CAAGAGTTAA | CCATGAGATT | GATTCACCCC | TTTAAGCCTC | CAAAGAAGTA | 420 |
| GTTGACTCAA | CGCATTTCGG | CATTTAAAAA | AGCCGAGAGC | AAATGAGACT | TTCCAGGAGA | 480 |
| AGGCACCAGG | GACATGAACA | ATTGATCGGC | TGACCAACTC | TATAAGAGAT | GCACCTCAAG | 540 |
| TTTGGGGATA | CTTATTCGGC | GTTTCTGGGG | ACAAATACGT | TCCCTATTGT | TGTATATAGG | 600 |
| TATTCGCACT | TAAGAAACAT | CTCTCATGGA | AAGAAGCTAG | GCGGAAAGGG | CGTTAAGTAC | 660 |
| TTGCCATTTA | ATCCTCAGCA | TCACTCGGAT | CAGTCGGAGA | TGTCGATGAA | AATGCACCAG | 720 |
| GAGCCGTGGA | GAGCAGCATG | GTAGAAAACA | ACGTAGCAAA | AAAGACGGTC | GCTAAAAAGA | 780 |
| CCGCACGCAA | GACCGCACGC | AAAGCAGCCC | CGCGCGTGGC | AACCCCATTG | GGAGTCGCAT | 840 |
| CTGAGTCTCC | CATTTCGG | | | | | 858 |

SEQ ID NO. 9:

| | | | | | | |
|---|---|---|---|---|---|---|
| TTACCGCAAG | CTCAATACGA | CTCACTATAG | GGGCCCGGTA | CCGAGCTCAC | TAGTTTAATT | 60 |
| AAAAGCTTAT | CGGCCTGAGG | TGAGAAGGGT | TCCGGACCCC | AGAATTCTCG | CGATAATTAA | 120 |
| TTAATAGCCC | GCCGTAATGA | GCGGGCTTTT | TTTTGATCCC | CGCCACCATA | ACCCACGAAT | 180 |
| CCTAACAAGT | CCCTGCATTC | TCGATGGCTT | TTTGGCTTTA | ATCCGTTTTG | GTTCAGGAAA | 240 |
| CTTACAAGAT | CTTTTACGCT | AGATGAAACT | TGCCATCGAA | CAGAATCCTG | CAGATGAAAT | 300 |
| CTTTCAGCAC | CATACATATC | GGTAATTCAT | AAAAATGCTCC | AGTGTCAAGC | TCTCGCAACG | 360 |
| TAATCGTTGC | TGTTCACGGA | GTTCTTACTA | GCTGCTCGGG | CGATCAATTT | GTCATTAGAT | 420 |
| TATGCAGTTA | TAGGGAGAAC | GGACACAAAA | GGGAGGGACC | TGACTGTACA | CTGTACTCCC | 480 |
| GCTAGCACGT | GTGTGGATG | ACACAGCTCA | GAAGCATTGC | AGTTGGACAA | CCCCTAGATA | 540 |
| AGACTGCGCA | AAGTAGGACA | TATCTCTCAC | TTTTCTTATT | GTTTTCGGGC | AAAACTAATC | 600 |
| CAGAACCTTT | CTAAAGGCCC | TGATCAATCA | GGATTTCTGC | GTGTCGACGT | GATGCCACAC | 660 |
| CTGCTTGGGC | AAGCACCTTC | TGCAGGCGAA | CTCCGTCAGA | GTCATTGCGG | CTTAAGAAAC | 720 |
| CCATCGACCA | ATCGTCGTCG | GATTTTACGT | TTTGCTTCTT | GGCAGGCTTA | GCGTTGGAGA | 780 |
| GAAGAATCTC | ATCCTTCTTC | TGAGGCTGCT | GGCGTGTGTT | TGGGCGGGAT | GATCCTGGCT | 840 |
| TGTAGCCACG | AACTGAAGAC | CGGTATCCGC | CAGAGCGATT | GCTCTGCTTC | TTGTCCGGTG | 900 |
| TGCCATCTCG | GCGAGCGGGT | GGGGTCACGT | AAGTGTCCTT | AATCTTGAGA | GAAAACGTAT | 960 |
| GAAATTGAAT | CCCGTGAATT | CTAGCCTATT | TTAGGAGATT | TTAATAGTCG | GGGCTTTAAC | 1020 |
| TGATGCTTTA | GAAGTCTTCA | TCAATGGAGT | CAACATCCGG | CAAAAGCGGT | GCTAGATCCG | 1080 |
| GTAATTTATC | CAAAGAATCA | ATACCCAACA | GCTCAAGCAG | GCAATTCCCG | TTGTGCCCAT | 1140 |
| AGCGGTGCGC | GCCCGTTGAT | TCGTCCACAT | CGACTTCTTT | GACTAGG | | 1187 |

SEQ ID NO. 10:

| | | | | | | |
|---|---|---|---|---|---|---|
| CTCAATTGCC | TCGTCTGAAG | GATGCTGACA | CTGAACTGAC | AGACGAGGAC | CGGGCCTAAG | 60 |
| ATTTTTTCGG | TGTATGGCGC | GGGCTGTGAG | GGGGATGTCG | TCGATAAGCG | TAGGGCCGAA | 120 |
| GAAGAAGCCC | TCCTCGTGCC | GTCTACGGCT | GCACGTTACG | CCGTCCACGA | CTGATCTTGG | 180 |
| CAGCCGGTCT | GGCCTCAGCG | ATGCGACATA | AGAAGCGACC | TTCTCGCGGT | GGCTGCGGTG | 240 |
| ATTAGTGGGC | CCAGGTCCGC | TCAGCCTGCT | CGCGCCGGCA | CCGTTGCCGA | TGCGAAGGGT | 300 |
| GTCGATGCGG | TCCTTGATCT | TCTCAATGAG | CTTTATTCCT | GGGCTTTGGG | AGCTTCAAAC | 360 |
| AGGAGGCATC | AAATTTGGGG | TAGTGCAGGG | CCTTTGAATC | CCACCTCACA | GATAGTATTC | 420 |
| AGGCATTTCC | TTGTCACGAT | GGTTTATCCT | TGGACACAAC | ATCAAAAGTG | GGGTACATCA | 480 |
| TATGCTTCCG | GTTGAAAGTG | ACCTATCTGA | AAAGACTTGG | CAGAACCTTA | AGCAATGGTG | 540 |
| TGAACTGCGT | TAACGAATTT | TGTCGGACGT | TAAAATGGCG | CATTCTGCTT | GCTAAGTGG | 600 |
| CACACCTATG | TGTTCTGCTT | GGGATAGCAG | TGCGGGAAAA | ATTTGAAAAA | GTCCGATTAC | 660 |
| CTTGAGGAGT | ATTCAATGTC | ATGACGCATT | GCTTCAGAAA | ACTGCGCTCC | AAG | 713 |

SEQ ID NO. 11:

| | | | | | | |
|---|---|---|---|---|---|---|
| CTGAAGGAGT | ACACCTTCGA | TCTGCTCTAC | AGATCTTTAG | TGATAACAGA | AACTCAGTAC | 60 |

-continued

| | | | | | | | |
|---|---|---|---|---|---|---|---|
| TCCGAAGATC | TCTACTGACA | GATCTTGGAT | GGACCCGAGG | ATGTTAAAGC | GATTCCCTTC | 120 |
| GCTACAACAG | CAACAAGGCC | CTCAACAACC | TTGGCTACGA | AGGACTCTTC | CCAGCGGATG | 180 |
| AAACCAAGGT | GTCCCCAAAC | ATCTTGTCTG | CGCTGTCACC | AAACGCTGAT | GAGAACCACG | 240 |
| ACTTCTTCTC | CGGCTCCGGT | TCCTCTTACG | TTATTGGTAA | GGCAGAAAAC | ACCCGAGGAT | 300 |
| GATGACCTGG | GACTTTCTAA | CTTTTAAAAA | GCTGAAGCGG | TCTACCGGCC | TGTAGGGTAA | 360 |
| CCTCAACCCG | TTAGAGCGTT | TTCGGGTTTC | CTGGTGGGGA | CTTAAAGGTG | CGGGGTTTTC | 420 |
| CGAAGCCGCA | ATATCAGGGG | TAAGGGACGA | CCAGGCACCC | CTGTGGCCCC | TCGGCAGCGC | 480 |
| ATCACGCTTT | AGGAGAAAAC | GCCCCTGGAA | TGGCGTCTCA | ACCATTCAGA | TTGAACCCCG | 540 |
| GCAGGGGGA | ATTATGAAAT | CTGTGACAGG | GGTTAACCGT | GGGGGTGGGC | TTCCTGGCAG | 600 |
| AAATGTCCGT | CAAATTGTGA | ACCCCTTCAC | ACCTTTGGTT | GAAAGCACTG | CCCACAAGTG | 660 |
| ACTGAACCTG | GCAGCGACCT | CATGAATTGT | TTGAAAAACA | TTTTTTTTGG | CACGAAAACG | 720 |
| GGGATACACG | TTAGCTGCAT | ACCAGCCTTT | TTGGGTTGCA | TCAGGATCCT | GCCTGTGGCC | 780 |
| TTATGATCAG | GCAGTGTTGT | TAAAGGACGA | TCGGTAATCC | GAATGGTTCG | TCCCGTAGTC | 840 |
| AGGAGGAACC | TATGACCGCT | GTGGCGCCTA | GGGTCGACGG | GCACGTGCCC | CTCTACGAGG | 900 |
| CCCGAGCCCG | ACAGGCCATG | CACGCAAGGG | CAGAAAGCAT | GGTTAATGAT | GACCACCACC | 960 |
| GGACCACAAG | CAGCTTGGGC | ATTATGTACA | TCATTATGTC | CTTCAG | | 1006 |

SEQ ID NO. 12:

| | | | | | | | |
|---|---|---|---|---|---|---|---|
| CTGCGTTGGC | CTTAAGGGAG | ATCACTTCAA | TTTCTTCATT | GTGAGGCAGC | CAGAACTCCA | 60 |
| CCACCTTTTC | CTGCTCTGAA | AGTCCATCCA | CTGTGAAGCA | CCTGCGGATC | TTCCAGACGC | 120 |
| CGTTCCGTGG | CGCCGGTGAT | GAAATTGACT | TCCGTGGTCT | CGCCCCCGGA | GGTTGGCGTG | 180 |
| GAAGATGTGG | GGGCGCCGTC | GATAAGCACA | TCAATCTTGC | CGCCCGGCCG | GCCGGAATCG | 240 |
| AGGTACACCA | CCGAGTGGAN | TACGTGGTCA | GCGTGAAGGA | GGTGGCGGTT | GGTGCGACAC | 300 |
| ACACGGCACG | CCCGTTGGTT | GGCGTTCCAT | CGCGCTAACT | TGGGATCACA | GTACGGTCTA | 360 |
| CTTATTCCTT | TGCTGAGCCA | ATCGGGCGAA | GGCCCCTTGT | TAGTGGTTCA | ATTTCGGTTG | 420 |
| CGCCGTGAAT | TAAATTCGGG | ATTTCATGAG | CTTAACCGTA | CCGCTCTTGC | AGAGTTCACA | 480 |
| GGGTAAACCC | TAAATGGAAC | AACCCATTGC | CAATATGTTG | GTTAAGTTGT | ACGCAAGTAA | 540 |
| ATCTTTTCAA | TCGTGGAAGC | AGGGCTCACA | GTCTAATGGC | ACGTATGCAG | GAAAGCGCCG | 600 |
| ATCTTCCAAA | TGTTCCTTCT | GCGGAAAGAG | CCAAAAGCAG | GTAAAAAAAC | TTCATCGCGG | 660 |
| GTGGCGCCGG | TATATATCTT | GTGATGAGTG | CATTGAGCTT | GTGCAACGAG | ATTATTGAAG | 720 |
| AAGAACTCAG | GTCAAGA | | | | | 737 |

The promoter DNA fragments of the present invention which includes any one of the above-listed nucleotide sequences and have a greater promoter strength than the tac promoter may not necessarily be a fragment isolated from naturally occurring chromosomal DNA of a coryneform bacteria, but may also be a fragment synthesized by a DNA synthesizer such as an Applied Biosystems model 380A DNA Synthesizer.

Some nucleotides of the above nucleotide sequence of the DNA fragment of the invention obtained from the chromosomal DNA of Brevibacterium flavum MJ-233 (FERMBP-1497) may be replaced with other nucleotides or deleted, or other nucleotides may be inserted into the sequences, as long as such nucleotide sequence changes will not substantially reduce the promoter strength of the DNA fragment which is greater than that of the tac promoter. Such DNA fragment derivatives are included in the promoter DNA fragment of the present invention.

Controllable Promoter DNA Fragment

Herein described will be a controllable promoter DNA fragment which is isolated from coryneform bacteria chromosomal DNA and functional in coryneform bacteria cells, wherein the promoter function of the controllable promoter DNA is controllable by replacing at least one substance which is contained in the culture medium and is assimilable by the host coryneform bacteria cells, with at least one other substance which is also assimilable by the host cells. The term "at least one substance which is contained in the culture medium and is assimilable by the host coryneform bacteria cells" means at least one of the substances necessary for coryneform bacteria to grow, such as carbon sources, nitrogen sources or other nutrients. Examples of such substances are glucose, fructose, ethanol, methanol, casein hydrolysates, yeast extracts, amino acids, urea, blackstrap molasses, and ammonium sulfate. Preferred among them are glucose, fructose, ethanol, casein hydrolysates and yeast extracts. Any single substance or any combination of several of such substances may be contained in a minimal medium. The concentrations of such substances in media may vary within such ranges that coryneform bacteria cells can use such substances to grow. Suitable concentrations of the preferred substances are: glucose, 5–0.01%; ethanol, 5–0.01%; fructose, 5–0.01%; casein hydrolysates, 1–0.01%; and yeast extracts, 1–0.01%. The term "minimal medium" means a medium consisting of substances which have known chemical structures and are essential for coryneform bacteria cells to grow. Examples of such essential substances to be contained in a minimal medium are: carbon sources, such as glucose and ethanol; nitrogen sources, such as ammonium, ammonium sulfate, ammonium chloride, ammonium nitrate and urea; inorganic salts, such as dipotassium hydrogenphosphate, potassium dihydrogenphosphate and magnesium sulfate; and other nutrients, such as biotin and vitamins.

A controllable promoter DNA fragment according to the present invention can be obtained as follows:

First, coryneform bacteria cells to which the above-described promoter probe shuttle vectors containing DNA fragments obtained from coryneform bacteria chromosomal DNA are introduced and are cultured in a minimal medium, followed by confirmation of the expression of the selectable marker gene by the above-described method. The transformants containing the promoter probe shuttle vectors are thus obtained. Secondly, each of the transformants is cultured in a minimal medium containing at least one of the above-described substances assimilable by coryneform bacteria cells, followed by confirming the expression of the reporter gene and determining the expression strength thereof. Then, each transformant is cultured in a minimal medium in which at least one substance that is assimilable by the host coryneform bacteria cells and contained in the minimal medium previously used is replaced with at least one other substance assimilable by the host coryneform bacteria cells, followed by confirming the expression of the reporter gene and determining the expression strength thereof. Thus, a transformant capable of controlling the expression of the reporter gene is obtained by replacing at least one substance that is contained in the medium and assimilable by the host coryneform bacteria cells with at least one other substance also assimilable by the host coryneform bacteria cells.

Methods for replacing at least one substance which is contained in the culture medium for the host coryneform bacterium cells and is assimilable by the host coryneform bacterium cells with at least one other substance which is assimilable by the host coryneform bacterium cells are not specifically restricted.

Such methods include;

1) cultivating cells in one medium containing one assimilable substance and collecting cells by centrifugation or by filtration, such methods known as usual and inoculating the collected cells to other medium containing other assimilable substance, or 2) cultivating cells in one medium containing an assimilable substance and adding another substance when one substance is almost completely utilized.

To determine whether the transformant's ability to control the expression of the reporter gene depends on the DNA fragments inserted into the promoter probe shuttle vector, that is, to eliminate the transformants which have acquired the ability to control the reporter gene expression due to mutations on their chromosomal DNA, plasmid DNA is extracted from each transformant and introduced again into other coryneform bacteria cells. The coryneform bacteria cells transformed with the plasmid DNA extracted from the transformant are examined to see whether the reporter gene expression strength in the cells changes when at least one substance that is assimilable by the cells and contained in the medium is replaced with at least one other substance assimilable by the cells, by the method as described above.

In this manner, a coryneform bacteria transformant harboring a promoter probe shuttle vector containing a promoter DNA fragment whose promoter function is controllable by replacing at least one substance that is contained in the medium and assimilable by the coryneform bacteria cells with at least one other substance assimilable by the coryneform bacteria cells can be obtained.

Examples of the transformants thus obtained are: the below-listed strains of *Brevibacterium flavum* MJ-233 which have been transformed with plasmids obtained by inserting AluI-HaeIII restriction fragments of chromosomal DNA of *Brevibacterium flavum* MJ-233 (FERM BP-1497) into the above-described promotor probe shuttle vector pPROBE17 at the restriction enzyme EcoRV recognition site, and which have the following characteristics. These transformants and the plasmids contained therein are named as follows.

(i) Transformants whose expression of the reporter gene is repressed by glucose contained in the media (the transformants become sensitive to kanamycin), and induced by replacing the glucose with ethanol (they become resistant to kanamycin concentrations of 100 µg/ml or greater):

| No. | Bacteria strain | Plasmid |
|---|---|---|
| (13) | *Brevibacterium flavum* MJ-233 KE101p | pPROBE17 KE101 |
| (14) | *Brevibacterium flavum* MJ-233 KE102 | pPROBE17 KE102 |
| (15) | *Brevibacterium flavum* MJ-233 KE103 | pPROBE17 KE103 |
| (16) | *Brevibacterium flavum* MJ-233 KE104 | pPROBE17 KE104 |

(ii) A transformant whose expression of the reporter gene is repressed by ethanol contained in the media (the transformant becomes sensitive to kanamycin), and induced by replacing the ethanol with glucose (it becomes resistant to a kanamycin concentration of 100 µg/ml or greater):

| No. | Bacteria strain | Plasmid |
|---|---|---|
| (17) | *Brevibacterium flavum* MJ-233 KG101 | pPROBE17 KG101 |

(iii) A transformant whose expression of the reporter gene is repressed by glucose contained in the media (that is, the transformant becomes sensitive to kanamycin), and induced by replacing the glucose with fructose (that is, it becomes resistant to a kanamycin concentration of 100 µg/ml or greater):

| No. | Bacteria strain | Plasmid |
|---|---|---|
| (18) | *Brevibacterium flavum* MJ-233 KF101 | pPROBE17 KF101 |

(iv) A transformant whose expression of the reporter gene is repressed by a combination of casein hydrolysates, yeast extracts and glucose contained in the media (the transformant becomes sensitive to kanamycin), and induced by replacing the combination of casein hydrolysates, yeast extracts and glucose with glucose (it becomes resistant to a kanamycin concentration of 100 µg/ml or greater):

| No. | Bacteria strain | Plasmid |
|---|---|---|
| (19) | *Brevibacterium flavum* MJ-233 KG102 | pPROBE17 KG102 |

(v) Transformants whose expression of the reporter gene is repressed by glucose contained in the media (the transformants become sensitive to kanamycin), and induced by replacing the glucose with a combination of casein hydrolysates, yeast extracts and glucose (they become resistant to kanamycin concentrations of 100 g/ml or greater):

| No. | Bacteria strain | Plasmid |
|---|---|---|
| (20) | *Brevibacterium flavum* MJ-233 KGYC101 | pPROBE17 KGYC101 |
| (21) | *Brevibacterium flavum* MJ-233 KGYC102 | pPROBE17 KGYC102 |
| (22) | *Brevibacterium flavum* MJ-233 KGYC103 | pPROBE17 KGYC103 |

The sizes and nucleotide sequences of the thus-obtained controllable promoter DNA fragments according to the present invention can be determined by the method as described above. Below listed are the sizes and nucleotide sequences of the DNA fragments inserted into the promoter probe shuttle vector pPROBE17 contained in the transformants isolated as described above. Table 2, 3 and 4 shows the sizes of the restriction fragments obtained by digesting with various restriction enzymes the DNA fragments inserted into the below-listed plasmid pPROBE17 KF101, pPROBE17 KGYC102 and pPROBE17 KGYC103 respectively. The sizes of the restriction fragments shown in Table 2, 3 and 4 were determined by agarose-gel electrophoresis.

Figure 6:
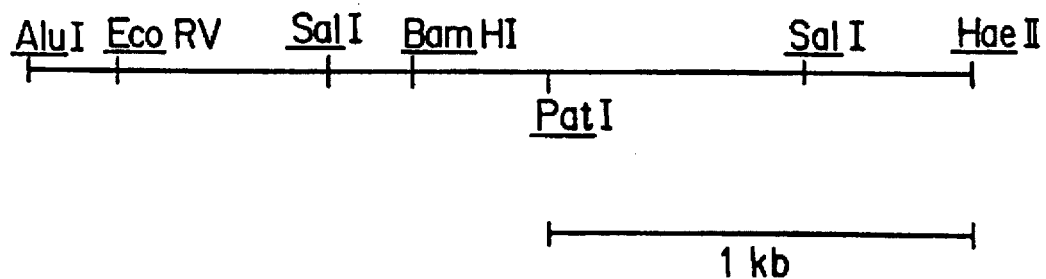
FIG. 6 shows a restriction map of a promoter DNA fragment whose promoter function is controllable by replacing the glucose with a combination of casein hydrolysates, yeast extracts and glucose in the culture medium for the host cell.
Figure 7:
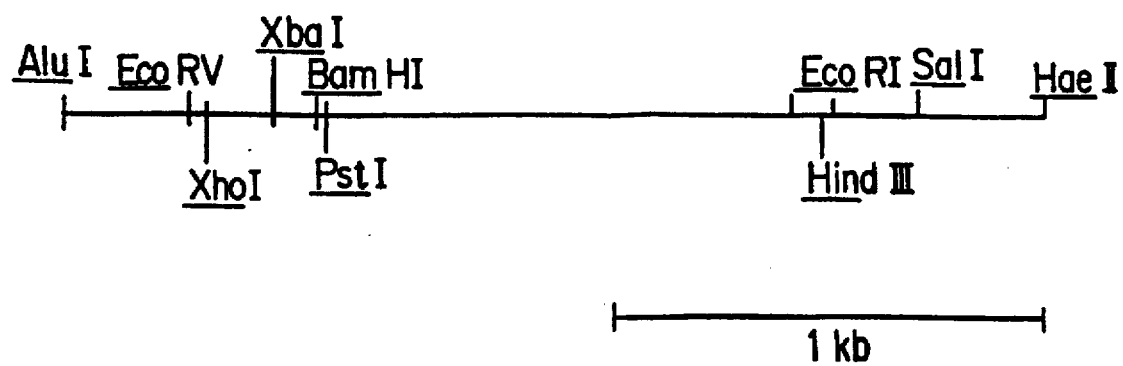
FIG. 7 shows a restriction map of a promoter DNA fragment whose promoter function is controllable by replacing the glucose with a combination of casein hydrolysates, yeast extracts and glucose in the culture medium for the host cell.

| No. | Plasmid | Size of insert DNA fragment | Sequence of insert DNA fragment |
|---|---|---|---|
| (13) | pPROBE17 KE101 | about 2,300 bp | SEQ ID No: 13 |
| (14) | pPROBE17 KE102 | about 550 bp | SEQ ID No: 14 |
| (17) | pPROBE17 KG101 | about 550 bp | SEQ ID No: 15 |
| (18) | pPROBE17 KF101 | about 2,500 bp | Table 2 (FIG. 5) |
| (19) | pPROBE17 KG102 | about 570 bp | SEQ ID No: 16 |
| (20) | pPROBE17 KGYC101 | about 1,110 bp | SEQ ID No: 17 |
| (21) | pPROBE17 KGYC102 | about 2,200 bp | Table 3 (FIG. 6) |
| (22) | pPROBE17 KGYC103 | about 2,300 bp | Table 4 (FIG. 7) |

SEQ ID NO. 13:

| | | | | | | |
|---|---|---|---|---|---|---|
| CTACTTCTTC | TTCACCGAAG | TATTCCTTAG | GGTCGATCTC | GTTACCCTCG | GAGTCCTTCA | 60 |
| CGTTTACGCG | GCAGATAGCC | TGTGCAAGAG | CCTTACGCACG | GCGAACGTCG | GAGAAGAGGT | 120 |
| TCGCGATCTG | GCCGGACTGC | TGCAGCTGAC | CGATGAACTG | GTTTGGGTCC | ATGCCGTAAG | 180 |
| ACTGTGCGGT | GAACAGGATG | TGGTCGGTGA | GCTCCTCGTG | CCGCTGATGC | GACTTCGAGT | 240 |
| CCGATCCAGC | CACCACCGAT | GAGGACCAGC | TTTTTACCTT | CACCGAAGTT | GCCTTGATCG | 300 |
| CGTCAGAGTC | TTCCACGGCG | CGCAGGTAGT | GCACATTAGA | GCCGTCGGCT | CCGGAATTGG | 360 |
| AAGTTTGCGA | CTGCTGAGCA | AGTAGCAAGA | ACTAGTTTGT | CGTAGTTAAT | GGTCTCAGTG | 420 |
| TTTCCGCCAT | CATCAACGGT | GACTTGGCGT | GAACCCGCAT | CAATTGCCGT | GACGCACACC | 480 |
| TTGACGCAGC | GTGACATTGT | TTTCTTTGTA | CCACCCCGCC | GGGTGAACAA | TCGCCTTTTC | 540 |
| AAAGCCTACT | TTTCCCGCCA | TGTACTCCTT | TGACACGCGT | GGGCGTTCAT | ATGGCAGATG | 600 |
| ATTTTCTGCT | GCGATGAGCG | TGATGGAGCC | TTCATGCCCG | TTTACACGCA | GTGCCTCTGC | 660 |
| GGTTTTCGCT | CCGGCTGAAC | CGCCGCCGAT | GATGACGATG | CTTTGTGGTG | TGCTCATGCT | 720 |
| GTACTCCTAG | TCCCTAAAAA | GTGGACGGTC | AGGCGCAAGG | TCGACCGCAT | GGTCTATACG | 780 |
| CCATGCTAGT | AAAAGGCCG | AAACCCTCGG | CGAGCGCGCT | AAATACCCGG | CCCCAATTGG | 840 |
| GGGTGTGAGG | CAGCACACAA | GACGAAACCC | TAACGAAATC | GCCAGACTCC | TCGCAATCAC | 900 |
| AAGAAGCGAC | GACTAGCCTG | TGGGGACAAA | CTATCTCAAG | AATTTATTCA | ACAAAGGAGT | 960 |
| TCTTCGCACA | TGAAGGAAGT | AGCAGTCAAC | GAAGTCCCAG | CAGGCGCGCA | GCTAATGCAC | 1020 |
| TGTCACTGTT | TCGACGTGAT | GTGCATCGGT | TTACGTGGTG | GCGTGGTTCA | CACATTGCTC | 1080 |
| CATCGGGCAT | TGGTGCGTCA | ATCGGTTTGG | GTTTTTAAGT | TTTGTGCGGG | GGTGGTCACC | 1140 |
| CCTGTTGTGA | ACTTTGCAAA | GTTATGACTT | CGCAGAAAAA | GTCGGCGGGG | GAGTTGCTAG | 1200 |
| TACGGATGTA | CTGGGCAAAT | GCTCTGAAAT | GGGAAAATGC | AGGCACCACA | ACTTTCCGTA | 1260 |
| GTTTTGAAGG | TGTGACCTAG | ATAAAAGTCG | GGGTTAGGCG | GGGGTAAATG | ACTAGGTAAA | 1320 |
| GGTTCGCAAA | CCCCCTTTTG | TTGGTGACGG | TGATCACTTA | GTCTGATCAC | ATCGCCAAAC | 1380 |
| ACGATAAGGG | TTGAAATCGA | AAGAAGAGCG | GCACCTAGAT | TCCAGAGGTA | GCCAGAGTGC | 1440 |
| TTTTCTTAAA | AGAGTTTTCA | CAACCGTTAA | CGGCGTAGCC | AAACAAGAAG | GATTCGCATT | 1500 |
| NCAGCTTCTG | GTTTAGGCAC | AGGTCATCTA | AAACCCATGC | TTTAAAAGGA | GCCTTCAATG | 1560 |
| ACTGAACAGG | AACTGTTGTC | TGCTCAGACT | GCCGACAACG | CTGGAACTGA | CAGCACCGAA | 1620 |
| CGCGTTGACG | CGGGCGGAAT | GCAGGTTGCA | AAAGTTCTCT | ACGACTTTGT | AACCGAAGCG | 1680 |
| GTACTCCCTC | GCGTGGGTGT | GGATGCGGAA | AAGTTCTGGT | CCGGATTCGC | CGCCATCGCC | 1740 |
| CGGGACCTCA | CCCCACGCAA | CCGCGAACTG | CTTGCTCGTC | GCGATGAACT | GCAGACGCTT | 1800 |
| ATCGACGACT | ACCACCGCAA | CAACTCCGGC | ACCATCGACC | AAGACGCGTA | CGAGGATTTC | 1860 |
| CTTAAAGAAA | TCGGATACTT | GGTTGAGGAG | CCAGAAGCTG | CAGAAATCCG | TACCCAAAAC | 1920 |
| GTCGATACGG | AAATCTCCAG | CACCGCAGAC | CTCAGCTGGT | TGTGCCAATT | CTGAACGCAC | 1980 |
| GTTCGCGCTG | AATGCTGCCA | ATGCTCGTTG | GGGTTCCCTC | TACGATGCGT | TGTACGGCAC | 2040 |
| CAACGCCATC | CCAGAAACTG | ATGGCGCTGA | AAAGGGCAAG | GAGTACAACC | CGGTCCGCGG | 2100 |
| CCAGAAGGTC | ATCGAGTCGG | GTCGTCAATT | CCTCGACAGC | GTTGTCCCAC | TGGACGGGTG | 2160 |
| CTTCGCATGC | CGATGTTGAG | AAGTACAACA | TCACGGATGG | AAA | | 2203 |

SEQ ID NO. 14:

| | | | | | | |
|---|---|---|---|---|---|---|
| CCTCATGGAT | GTTGACATCG | ATATGGATTC | CGACATCTGA | GCAGATCCTC | TCCTGGCGGA | 60 |
| CACAGACGCA | TCCCTGCTCT | CCCTGGAAGC | TGGCACCTGT | GACCGTTGCC | TTCGACACGA | 120 |
| CACATGCTGA | CCACCCTGGA | GAACTCCGGC | CTATCGTGCC | GATCGTTCCA | GGCGCTGTGA | 180 |
| TTTTTGATTT | GTTGGTGGGC | GATCCCAAAA | ACAGGCCGCT | GAGAAAGTTT | TCCACACTAA | 240 |
| AATAGTGTGA | TTCTGCCGAA | TCTGTTGTTT | TACTTTTGAA | ACTGCGGGAT | CATGAAAAGT | 300 |
| AGTGAAAAGT | GAATTTTAGT | TCTGTGCTTT | CTCTTCCCTT | TAAGTGAACC | TTTTGTTGGA | 360 |
| TCTTCATTAA | AAAAATGAAA | ACCTCGTCGG | AATGCAACTT | GGGATCACTG | TCTCGGGCAA | 420 |
| GAAACGGCCT | TAAAAAAGGG | GAGTGATTGT | GAGTGCTTGA | TTTCTTAGCT | GCGAACCCGC | 480 |
| TTGATTGCTG | CTTGGTGGTT | ATTTTGGCCA | CGGGTGACCA | CTCCCAGACT | CAGCTGCCAG | 540 |
| GTGGTCAGTG | G | | | | | 551 |

SEQ ID NO. 15:

| | | | | | | |
|---|---|---|---|---|---|---|
| GATCCTCATG | GATGTTGACA | TCGATATGGA | TTCCGACATC | GAGCAGATCC | TCTCCGGCGG | 60 |
| ACACGACGCA | TCCCTGCTCT | CCCTGGAAGC | TGGCACCTGT | GACGTTGCCT | TCGCACACGA | 120 |
| CACCATGCTG | ACCACCCTGG | AGAACTCCGG | CCTATCGTGC | CGATCGTTCC | AGGCGCTGTG | 180 |
| ATTTTTGATT | TGTTGGTGGG | CGATCCCAAA | AACAGGCCGC | TGAGAAAGTT | TTCCACACTA | 240 |
| AAATAGTGTG | ATTCTGTCCG | AATCTGTTGT | TTTAGTTTTG | AAACTGCGGG | ATCATGGAAA | 300 |
| GTAGTGAAAA | GTGAATTTTA | GTTCTGTGCT | TTCTCTGCCC | TTTAAGTGAA | CCTTTTGTTG | 360 |
| GATCTTGCAT | TAAAAAAATG | AAAACCTCGT | CGGGAATGCA | ACTTGGGATC | ACGTCTCGGG | 420 |
| CAAGAAACGT | CCTTAAAAAA | GGGGAGTGAT | TGTGAGTGCT | TGATTTCTTA | GCTGCGAACC | 480 |
| CGCTGATTGC | GCTGGTGGTT | ATTTTGGCCA | CGGGTGACCAC | TCCCGACTCG | GCGCCGGTGG | 540 |
| TCGTGGATC | | | | | | 549 |

SEQ ID NO. 16:

| | | | | | | |
|---|---|---|---|---|---|---|
| GATCCAAAAA | GTCGGCGCAG | CTGACTGGAG | CTTCTGGGAA | GCCAAAGTCC | GCGCCCGCGA | 60 |
| CTACGCCCTG | GACGAAACCG | AACTGCGCAA | CTACTTCCCA | CTGAACCAAG | TACTCTGTGA | 120 |
| CGGCGTCTTC | TTCGCTGCTA | ACCGCCTCTA | CGGAATCACC | GTGGAACCAC | GCCCTGACCT | 180 |

-continued

```
GCGCGGTTAC  GCCGAGGGCG  TGGACGTCTG  GGAAGTCCTC  GATTCTGACG  GCTCCGGCAT   240
CGGCCACAAG  TGCGATGCGC  CCCTTCCGGG  TCGGCGAGGC  GGTGATCTTG  CGGTGTCTAC   300
CTGGGGTCGA  CTGTCGAGTC  GTGGTCCGCA  TTGAACTTCT  TTCCGTGGTG  TTTATCTTTT   360
CATCACAAAC  AATCACGACG  GTATACCCAT  CGGAGACGAT  ATCGTGATCT  TTCTGTTACC   420
TGCGGAAGGT  AACATTAGTA  TTTCAACTCG  ACAGAGTCCA  TCCTGGAAGC  GTGTATGACG   480
ATTTCTTCAC  ACATTCTTTA  CAATGGCCTT  TCGTGCGATA  ATGCTAGGCA  TGCTTCGATG   540
GACTACAGCA  GGTGAATCCC  ACGGATC                                         567
SEQ ID NO. 17:

CTGGTTTTGG  CGGTAGGCAA  ACATGCCTTT  GAGGGTAGAT  GCCGGTAGGC  GGAGTGCTCA    60
CGGAATCTGT  GATGAGTGTG  CCGCCGTCTT  GGTCGATGAA  ATTGTGCACG  TGACGCCAGT   120
TTGCGAGGGC  CTTTACGGGG  GCGGTCAGAC  AGACGTCGGT  GAAGCGTGAA  CCATTCAAAA   180
ATCCCGATAA  ATCATGGCGC  GCCACCCATT  TAAGTCCCGC  AGGAAGGCTG  AAAATGGTGG   240
TGCCATCGGA  GAGGCGTTCT  GCCTGCGCAA  TGGGGTTAAG  GGGGACGAAT  GGCGGAGTCA   300
GACGTGTGAC  AGCGCCCTTA  CGGGTATGCC  AATCCCAGAC  CATTTCTCGG  GGAAAAGGAA   360
TAAAATGGCT  TGTGGTCAGA  CTCACAGGGG  CTTCTCCAAG  TCAGTGGATT  TATGAGGTCC   420
CAGTGGGTAC  ACACCGGGTG  TCCTACAACG  ATCAATTGTC  ACAGATTCGA  CTGGCATGCT   480
GTACCATCTG  CTTTAAGCAT  TTTGGTGTTT  CACTGTTGTT  AACAGTGTTT  CACCGTGGAG   540
CACTACCTAA  AGATCATAGT  CAGCATCTTG  GACACGGTAC  GCTATAGTGT               600
CAGACAACAA  CCAGGAAACT  GGTCGTTGCA  GAGTTTTTGC  AAAATTGGAC  ATCCTTTAAC   660
GGACCGCACA  GAGAGGCGGG  AAGGAGGTCA  CGATGAGCGA  ACGTAATAGT  GCTGTACTAG   720
AACTCCTCAA  TGAGGACGAC  GTCAGCCGTA  CCATCGCACG  CATCGCGCAC  CAGATTATTG   780
AGAAAACCGC  GCTTGATTCC  AAATACGCGG  ATCGGGTCAT  GTTGTTAGGC  ATTCCTTCAG   840
GTGGAGTCCC  GCTGGCCCGA  AGGCTTGCTG  AAAAGATCGA  AGAATTTTCC  GGCGTTTCGG   900
TAGATACCGG  CGCTGTTGAT  ATCACCTTGT  ACAGGGATGA  TCTTCGAAAC  AAACCGCACC   960
GCGCACTGCA  GCCCACCTCT  ATTCCGGCAG  GTGGTATCGA  TAACACCACC  GTGATTTTGG  1020
TGGATGATGT  GCTGTTTTCC  GGTCGTACTA  TNCGCGCTGC  ACTTGATGCA  TTGCGCGACG  1080
TTGGACGCCC  AAACTATATC  CAATTAG                                        1107
```

TABLE 2

| Restriction enzyme | Number of restriction enzyme recognition site | Size of restriction Fragment (bp) |
|---|---|---|
| EcoRI | 1 | 2000, 500 |
| EcoRV | 1 | 2200, 300 |
| BamHI | 1 | 1900, 600 |
| PstI | 1 | 1850, 650 |
| KpnI | 0 | 2500 |
| HindIII | 1 | 1700, 800 |
| SalI | 1 | 2300, 200 |
| XbaI | 1 | 2000, 500 |
| XhoI | 2 | 2100, 400 |

TABLE 3

| Restriction enzyme | Number of restriction enzyme recognition site | Size of restriction Fragment (bp) |
|---|---|---|
| EcoRI | 1 | 2200 |
| EcoRV | 1 | 2000, 200 |
| BamHI | 1 | 1300, 900 |
| PstI | 1 | 1200, 1000 |
| KpnI | 0 | 2200 |
| HindIII | 1 | 2200 |
| SalI | 1 | 1100, 700, 400 |
| XbaI | 1 | 2200 |
| XhoI | 2 | 2200 |

TABLE 4

| Restriction enzyme | Number of restriction enzyme recognition site | Size of restriction Fragment (bp) |
|---|---|---|
| EcoRI | 1 | 1800, 500 |
| EcoRV | 1 | 2000, 300 |
| BamHI | 1 | 1700, 600 |
| PstI | 1 | 1700, 600 |
| KpnI | 0 | 2300 |
| HindIII | 1 | 1800, 500 |
| SalI | 1 | 2000, 300 |
| XbaI | 1 | 1800, 500 |
| XhoI | 2 | 2000, 300 |

The controllable promoter DNA fragment of the invention including the above nucleotide sequences and DNA fragment may not necessarily be obtained from naturally occurring coryneform bacteria chromosome DNA, but may also be synthesized by a known DNA synthesizer, such as an Applied Biosystems model 380A DNA Synthesizer.

Some nucleotides of controllable promoter DNA fragments according to the invention obtained from chromosomal DNA of Brevibacterium flavum MJ-233 (FERMBP-1497) may be replaced with other nucleotides or deleted, or other nucleotides may be inserted into the sequences of the DNA fragments, as long as such nucleotide sequence changes will not substantially reduce the promoter control capability of the DNA fragments. Such DNA fragment derivatives are included in the controllable promoter DNA fragment of the present invention.

A gene of interest can be expressed at a high rate and efficiency in coryneform bacteria cells by using a coryneform bacteria promoter DNA fragment according to the invention, more specifically, by ligating the gene to the downstream end of the promoter DNA fragment, inserting the ligated fragments into plasmid vectors which can replicate by themselves in coryneform bacteria cells, and then introducing the plasmid vectors into coryneform bacteria cells. The gene of interest to be ligated to the downstream end of the promoter DNA fragment of the invention may be a variety of genes including microorganism genes, animal genes, plant genes and synthetic genes. Examples of gene expression products include: enzymes involved in the biosynthesis and metabolism of bio-substances, such as amino acids, organic acids, vitamins, and lipids; and enzymes involved in the biosynthesis and metabolism of bioactive substances, such as proteins, fats and oils, and antibiotics. A plasmid vector used to carry a promoter DNA fragment according to the present invention may be any type that has a plasmid replication origin DNA region functional in coryneform bacteria cells. Examples of such plasmid vectors are:

(1) pAM330 [Agricultural and Biological Chemistry., 48. 2901, (1986)]

(2) pCG4 [Journal of Bacteriology., 159, 306, (1984)]

(3) pSR1 [Journal of Bacteriology., 162, 591, (1985)]

(4) pBY503 [Journal of Industrial Microbiology, 5, 159, (1990)]

(5) pBL1 [Journal of Bacteriology., 162, 463, (1985)]

(6) pHM1519 [Gene., 39, 281, (1985)]

(7) pCG1 [Molecular and General Genetics., 196, 175, (1984)]

(8) pCG100 [Journal of General Microbiology., 137, 2093, (1991)]

Further, plasmid vectors having plasmid replication origin DNA region functional in coryneform bacteria cells which are obtained from any one or more of the above-listed plasmid vectors can also be suitably used.

The present invention will be further described in detail with reference to Examples hereinafter. The following Examples are intended to be illustrative, and should not be construed as limiting the claimed invention.

EXAMPLES

Example 1

Construction of Promoter Probe Shuttle Vector pPROBE17

Figure 2:
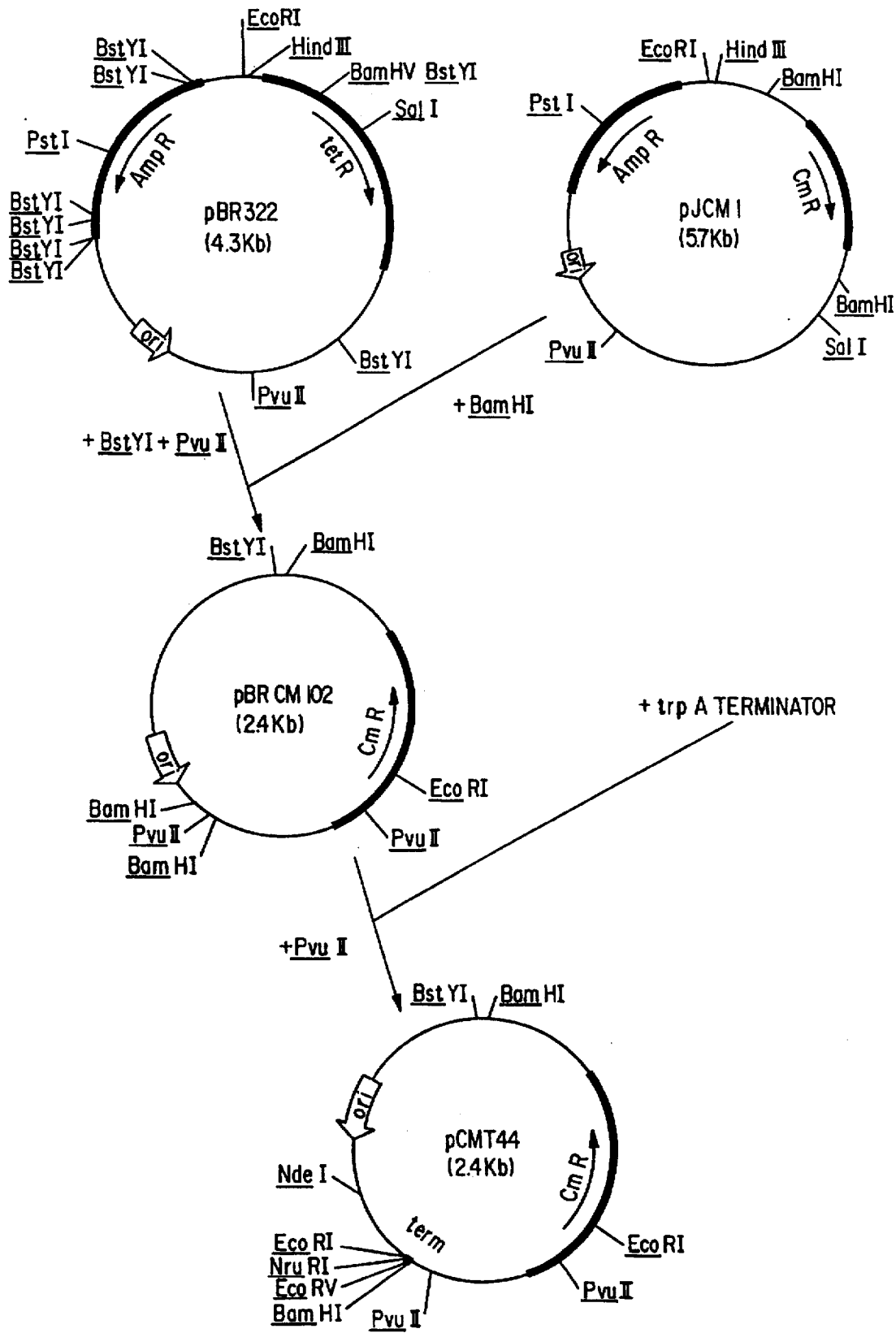
FIG. 2 shows the construction of two specific vectors, namely, pBRCM102 and pCMT44, constructed in accordance with this invention.
Figure 3:
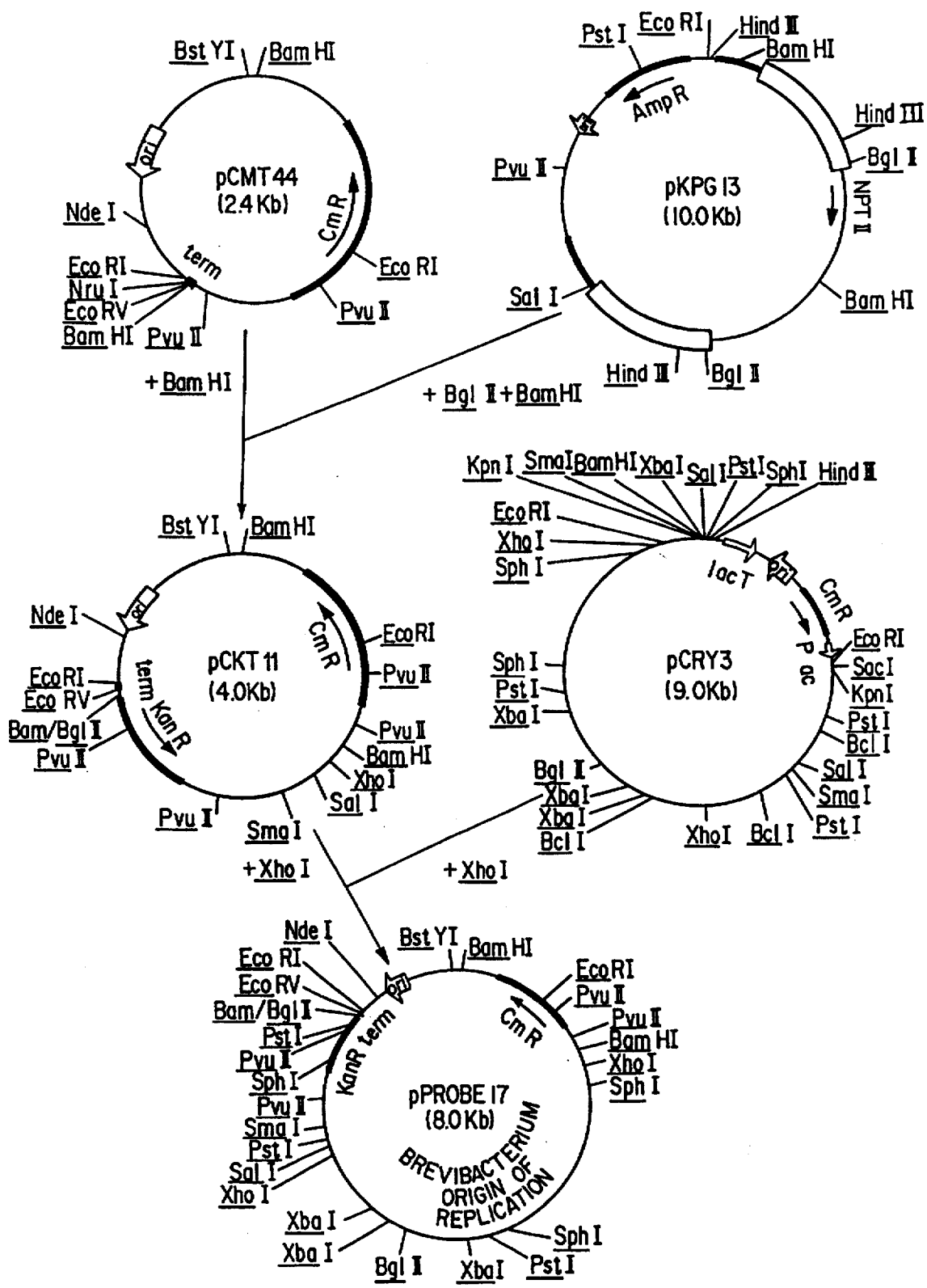
FIG. 3 shows the construction of two specific vectors, namely, pCKT11 and pPROBE17, constructed in accordance with this invention.
Figure 4:
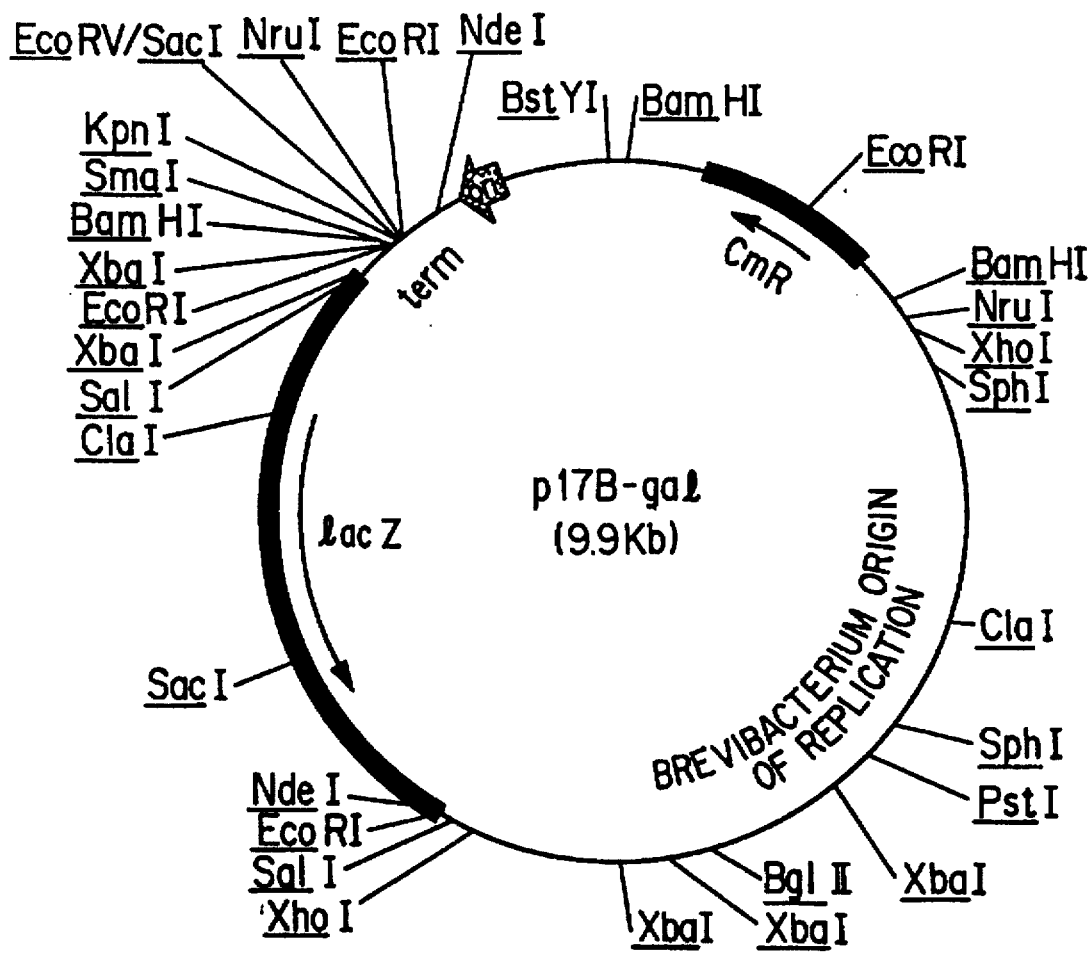
FIG. 4 shows a specific novel plasmid vector 17Bgal useful for detecting promoter DNA fragments in coryneform bacteria.

Promoter probe shuttle vector pPROBE17 was constructed by the scheme illustrated in FIGS. 2 and 3.

First, a plasmid, named as pBRCM102, as shown in FIG. 2 was constructed as follows:

10 μg of *Escherichia coli* plasmid pBR322 DNA was digested by incubating with the restriction enzymes PvuII and BstYI at 37° C. for one hour, followed by separating the resultant fragments by agarose-gel electrophoresis. A 1.1 Kb DNA fragment including a DNA region (ORI) involved in the plasmid replication in *Escherichia coli* cells was eluted from a gel section containing the fragment, and then purified, thus obtaining 1.5 μg of DNA.

37° C. for one hour, thus obtaining a DNA fragment (the region a) having a BamHI site at the 5' end.

Separately, 1 g of plasmid pJCM1 DNA having a chloram-phenicol resistance gene of the transposon Tn9 was digested by incubating with the restriction enzyme BamHI at 37° C. for one hour, thus obtaining a region c DNA fragment.

After the region c DNA fragment and the region a DNA fragment were separately incubated at 60° C. for 10 minutes, they were mixed and then ligated by incubating the mixture with the T4 DNA ligase at 16° C. for 24 hours in the presence of ATP and dithiothreitol.

The ligation products were introduced into *Escherichia coli* HB101 (Takara Shuzo Co., Ltd.) by the calcium chloride method (Journal of Molecular Biology, 53,159 (1970)). The cells were then plated on a selective agar plate (prepared by dissolving 10 g of tryptone, 5 g of yeast extracts, 5 g of sodium chloride and 16 g of agar into distilled water to obtain 1 liter) containing 50 mg/l of chloramphenicol.

Then, plasmid DNA was extracted from the colonies on the selective agar plate by an usual method (Nucleic Acids Research, 9, 1989 (1981)), and digested with various restriction enzymes. The restriction fragments were electrophoresed on a agarose gel, thus confirming that a plasmid pBRCM102 as shown in FIG. 2 was obtained.

Secondly, a plasmid, named as pCMT44, as shown in FIG. 2 was constructed using the plasmid pBRCM102 as follows:

5 μg of the plasmid pBRCM102 DNA was partially digested by incubating with the restriction enzyme PvuII at 37° C. for 5 minutes.

Separately, single-strand DNA fragments of the following DNA fragment with the following sequence, that is, the trans-cription terminating element trpA terminator (region e, hereinafter referred to as "the term") of the *Escherichia coli* tryptophan operon, were separately synthesized by using an Applied Biosystems model 380A DNA synthesizer.

(3) 5' AATTCTCGCGATAATTAATTAATAGCCCGCCTAATGAGCGGGCTTTTTTTTGATATCAATT 3'   (SEQ ID No. 18)
(4) 3' TTAAGAGCGCTATTAATTAATTATCGGGCGGATTACTCGCCCGAAAAAAAACTATAGTTAA 5'

The thus-obtained DNA fragment lacked the RNAI promoter region, that is, a pBR322 replication control element. To provide promoters for the DNA fragments, a synthetic DNA fragment having promoter function was synthesized as follows. Single-strand DNA fragments (1) and (2) of the following DNA fragment (containing a restriction enzyme BamHI recognition site) were separately synthesized by using an Applied Biosystems model 380A DNA synthesizer.

The single-strand DNA fragments were mixed and then annealed by incubating the mixture at 50° C. for 5 hours, thus obtaining 5 μg of double-strand DNA having the sequence shown above.

5 μg of the synthesized DNA and 5 μg of the plasmid DNA partially digested with restriction enzyme PvuII were mixed and then ligated by incubating the mixture with the DNA ligase at 16° C. for 24 hours in the presence of ATP and dithiothreitol.

(1) 5' GATCTCAAGA  AGATCCTTTG  ATCTTTTCTA  CGGATCCCAG  3' (SEQ ID NO. 21)
(2) 3'           AGTTCT      TCTAGGAAAC  TAGAAAAGAT  GCCTAGGGTC  5'

The single-strand DNA fragments (1) and (2) were mixed and then annealed by incubating the mixture at 50° C. for 5 hours, thus obtaining 5 μg of double-strand DNA as shown above.

Then, 5 μg of the double-strand DNA and 1.5 μg of the 1.1 Kb DNA were mixed and then ligated by incubating the mixture with the T4 DNA ligase at 16° C. for 24 hours in the presence of ATP and dithiothreitol. The ligation product was digested by incubating with the restriction enzyme BamHI at The ligation products were introduced into *Escherichia coli* HB101 (Takara Shuzo Co., Ltd.) by the sodium calcium method (Journal of Molecular Biology, 53, 149 (1970)), followed by plating the cells on a selective agar plate (prepared by dissolving 10 g of tryptone, 5 g of yeast extracts, 5 g of sodium chloride and 16 g of agar into distilled water to obtain 1 liter) containing 50 mg/l of chloramphenicol.

Then, plasmid DNA was extracted from the colonies on the selective agar plate by an usual method (Nucleic Acids Research, 9, 1989 (1981)), and digested with various restriction enzymes. The restriction fragments were electrophoresed on an agarose gel, thus confirming that a plasmid pCMT44 was obtained. As shown in FIG. 2, the plasmid pCMT44 contains the transcription terminating element trpA terminator (region e) at the PvuII site in the downstream from the replication-related DNA region (ORI), that is, in a region closer to the 3' end of the ORI region.

Third, a plasmid, named as pCKT11, as shown in FIG. 3 was constructed using the plasmid pCMT44 as follows:

10 μg of plasmid pKPG13 DNA was digested by incubation with the restriction enzymes BglII and BamHI at 37° C. for one hour, so that the desired restriction fragment would not include the promoter of the kanamycin resistance gene. The restriction fragments were electrophoresed on an agarose gel, followed by cutting out a gel section exclusively containing a 1.5 Kb kanamycin resistance structural gene fragment. The DNA fragment was eluted from the gel section and purified, yielding 1 μg (region d, i.e., the reportergene).

1 μg of the thus-obtained DNA was mixed with the restriction fragments obtained by partially digesting 1 μg of the plasmid pCMT44 DNA with the restriction enzyme BamHI at 37° C. for 5 minutes. The mixture as incubated at 16° C. for 24 hours in the presence of the T4 DNA ligase, ATP and dithio-threitol to ligate the DNA fragments.

The ligation products were introduced into *Escherichia coli* HB101 (Takara Shuzo Co., Ltd.) by the sodium calcium method (Journal of Molecular Biology, 53, 149 (1970)), followed by plating the cells on a selective agar plate (prepared by dissolving 10 g of tryptone, 5 g of yeast extracts, 5 g of sodium chloride and 16 g of agar into distilled water to obtain 1 liter) containing 50 mg/l of chloramphenicol.

Then, plasmid DNA was extracted from the colonies on the selective agar plate by a known usual method (Nucleic Acids Research, 9, 1989 (1981)), and digested with various restriction enzymes. The restriction fragments were electrophoresed on a agarose gel, thus confirming that a plasmid pCMT11 as shown in FIG. 3 was obtained.

Finally, a plasmid, named as pPROBE17, as shown in FIG. 3 was constructed using the plasmid pCKT11 as follows:

Plasmid DNA was extracted from *Brevibacterium flavum* MJ-233 GE102 (FERM BP-2513) containing the plasmid pCRY3 capable of replication in coryneform bacteria cells, by a usual method (Nucleic Acids Research, 9, 1989 (1981)). 10 μg of the plasmid DNA was incubated with the restriction enzyme XhoI at 37° C. for one hour. The resultant restriction fragments were electrophoresed on an agarose gel, followed by cutting out a gal section containing a 4.0 Kb DNA fragment capable of replication in coryneform bacteria cells. The DNA was eluted from the gel section and purified, yielding 2.5 μg (region b).

2.5 μg of the DNA fragment and 1 μg of the plasmid pCKT11 DNA were separately incubated with the restriction enzyme XhoI at 37° C. for one hours. After the resultant restriction fragments were mixed and incubated at 65° C. for 10 minutes, the mixture was incubated at 16° C. for 24 hours in the presence of the T4 DNA ligase, ATP and dithiothreitol to ligate the fragments.

The ligation products were introduced into *Escherichia coli* HB101 (Takara Shuzo Co., Ltd.) by the sodium calcium method (Journal of Molecular Biology, 53, 149 (1970)), followed by plating the cells on a selective agar plate (prepared by dissolving 10 g of tryptone, 5 g of yeast extracts, 5 g of sodium chloride and 16 g of agar into distilled water to obtain 1 liter) containing 50 mg/l of chloramphenicol.

Then, plasmid DNA was extracted from the colonies on the selective agar plate by a known method (Nucleic Acids Research, 9, 1989 (1981)), and digested with various restriction enzymes. The restriction fragments were electrophoresed on a agarose gel, thus confirming that a plasmid pPROBE17 as shown in FIG. 3 was obtained.

The plasmid pPROBE17 consists essentially of:

a) a plasmid replication origin region functional in *Escherichia coli*, b) a plasmid replication origin region functional in coryneform bacteria, c) a chloramphenicol resistance gene, d) a kanamycin resistance gene lacking its own promoter, and e) a transcription terminating element trpA terminator present in the upstream of the kanamycin resistance gene.

Example 2

Introduction of Plasmid pPROBE17 into Coryneform Bacteria Cells

*Brevibacterium flavum* strain MJ-233 (FERM BP-1497) was cultured in A medium (prepared by dissolving 2 g of urea, 7 g of (NH4)2SO4, 0.5 g of K2HPO4, 0.5 g of KH2PO4, 0.5 g of MgSO4, 6 mg of FeSO4 7H2O, 6 mg of MnSO4 4–6H2O, 2.5 g of yeast extracts, 5 g of casamino acid, 200 μg of biotin, 200 μg of thiamin hydrochloride and 20 g of glucose into distilled water to obtained 1 liter) at 33° C. until the logarithmic metaphase, followed by adding penicillin G to the medium so as to obtain a concentration of 1 unit/ml. After being further cultured for 2 hours, the cells were collected by centrifugation. The obtained bacterial cells were washed with sterilized water and a pulse buffer (272 mM sucrose, 7 mM KH2PO4, 1 mM MGCl2, pH 7.4) followed by centrifugation. The washed bacterial cells were suspended in 2 ml of the pulse buffer. 120 μl of the bacterial cells suspension were mixed with 5 μg of the plasmid pPROBE17 DNA obtained in Example 1, and the mixture was allowed to stand in ice for 10 minutes. After the mixture was pulsed by a Gene Pulser (BioLad) at 1950 V and 25 μFD, the mixture was allowed to stand in ice for 10 minutes. The entire mixture was suspended in 3 ml of A medium, followed by incubation at 33° C. for one hour. The mixture was plated on an A-medium agar plate (the A medium-agar proportion being 1 liter to 16 g) containing 3 g/ml (final concentration) of chloramphenicol, and incubated at 33° C. for 2 days. Plasmid DNA was extracted from the colonies of chloramphenicol resistant strains by a known usual method (Nucleic Acids Research, 9, 1989 (1981)), and digested with various restriction enzymes. The restriction fragments were electrophoresed on a agarose gel, thus confirming that the extracted plasmid was the plasmid pPROBE17 constructed in Example 1 as shown in FIG. 3.

Because the plasmid pPROBE17 does not have a promoter region of the kanamycin resistance gene, the coryneform bacteria cells transformed with only the plasmid are expected to exhibit no resistance to kanamycin.

To confirm this, such coryneform bacteria cells were plated on an A-medium agar plate as described above and incubated at 33° C. for 4 days. As a result, no colony was observed on the plate. Thus, it was proven that the transcription terminating element trpA terminator present in the upstream from the kanamycin resistance gene on the plasmid pPROBE17 is effective. In other words, there is no expression of the kanamycin gene caused by read-through on the plasmid pPROBE17 in coryneform bacteria cells.

Example 3

Strength of *Escherichia coli* tac Promoter in Coryneform Bacteria Cells tac Promoters were isolated from the plasmid pDR540 (Pharmacia Co., Ltd.) as follows:

25 µg of the plasmid pDR540 DNA was incubated with the restriction enzymes HindIII and BamHI at 37° C. for one hour. The resultant restriction fragments were electrophoresed on an agarose gel, followed by cutting out a gel section containing a DNA fragment containing a 96 bp tac promoter. The DNA was eluted from the gel section and purified, yielding 0.5 µg. 2.5 µg of the obtained DNA fragments were incubated with the S1 nuclease at 37° C. for one hour to blunt the both ends of the fragments. Separately, 0.5 µg of the plasmid pPROBE17 DNA was incubated with the restriction enzyme EcoRV at 37° C. for one hour. The ends of the resultant restriction fragments were blunted in a similar manner.

These blunt-end DNA fragments were incubated at 65° C. for 10 minutes, and then these DNA fragments were ligated by incubation at 16° C. for 24 hours in the presence of the DNA ligase, ATP and dithiothreitol.

The ligation products were introduced into *Brevibacterium flavum* MJ-233 (FERM BP-1497) by the sodium calcium method (Journal of Molecular Biology, 53, 149 (1970)). The transformants were selected by plating the resultant bacterial cells on an A-medium agar plate containing 30 µg/ml (final concentration) of kanamycin and then incubating at 33° C. for 2 days.

Then, plasmid DNA was extracted from the kanamycin resistant strain colonies by a known method (Nucleic Acids Research, 9, 1989 (1981)), and digested with various restriction enzymes. The restriction fragments were electrophoresed on a agarose gel, thus confirming that a 270 bp DNA fragment containing a tac promoter had been inserted into the plasmid pPROBE17 at the EcoRV site.

To determine the strength of the tac promoter in coryneform bacteria cells, the thus-obtained kanamycin resistant strain was plated on A-medium agar plates (as described above) containing different concentrations of kanamycin and incubated at 33° C. for 4 days. As a result, the strain was able to grow on an A-medium agar plate containing 100 µg/ml (final concentration) of kanamycin, but failed to grow on an A-medium agar plate containing 500 µg/ml of kanamycin.

Example 4

Preparation of Coryneform Bacteria Chromosomal DNA

*Brevibacterium flavum* strain MJ-233 (FERM BP-1497) was cultured in A medium at 33° C. until the logarithmic phase, followed by centrifugation to collect the cells. The obtained bacterial cells were suspended in 15 ml of a lysozyme reaction mixture (10 mg/ml lysozyme, 10 mM NaCl, 20 mM Tris-HCl (pH 8.0), 1 mM EDTA-2Na). Subsequently, the proteinase K was added to the lysozyme reaction mixture to a final concentration of 100 µg/ml, followed by incubation at 37° C. for one hour. Then, sodium dodecyl sulfate was added to the mixture to a final concentration of 0.5%, followed by incubation at 50° C. for one hour to promote cell lysis. The lysate was added to an equal volume of a phenol-chloroform (1:1, by v/v) solution, and moderately shaken at room temperature for 10 minutes. The entire mixture was then centrifuged, and a supernatant fraction was recovered. After adding sodium acetate to the recovered supernatant fraction to a concentration of 0.3M, ethanol was added to the mixture (the ethanol-mixture volume ratio being 2:1), followed by centrifugation. The precipitated DNA was washed with 70% ethanol and dried. The dried DNA was dissolved into 5 ml of a solution containing 10 mM Tris-HCl (pH 7.5) and 1 mM EDTA-2Na, thus obtaining a coryneform bacteria chromosomal DNA solution.

Example 5

Isolation of Promoter DNA Fragment Having Greater Promoter Strength Than tac Promoter from Coryneform Bacteria Chromosomal DNA 20 µg of the coryneform bacteria chromosomal DNA prepared in Example 4 was completely digested by incubation with the 4-base-sequence recognizing restriction enzymes AluI and HaeIII at 37° C. for 10 hours. Separately, 10 µg of the plasmid pPROBE17 DNA prepared in Example 2 was digested by incubation with the restriction enzyme EcoRV at 37° C. for one hour. After these resultant solutions were incubated at 65° C. for 10 minutes, they were mixed and then incubated at 16° C. for 24 hours in the presence of the T4 DNA ligase, ATP and dithiothreitol to ligate the DNA fragments.

The ligation products were introduced into *Brevibacterium flavum* strain MJ-233 (FERM BP-1497) by the method described in Example 2. The transformants were selected by plating the resultant bacterial cells on A-medium agar plates containing various concentrations of kanamycin: 500, 750, 1000, 1500 µg/ml (final concentrations) and then incubating at 33° C. for 3 days. As a result, twelve transformants capable of growing on media containing 500 µg/ml or more of kanamycin were obtained, as shown in Table 1. These transformants and their plasmids are named as follows:

| No. | Bacteria strain | Plasmid |
|---|---|---|
| (1) | *Brevibacterium flavum* AAJ-233 Km5001 | pPROBE17 Km5001 |
| (2) | *Brevibacterium flavum* MJ-233 Km5002 | pPROBE17 Km5002 |
| (3) | *Brevibacterium flavum* MJ-233 Km5003 | pPROBE17 Km5003 |
| (4) | *Brevibacterium flavum* MJ-233 Km5004 | pPROBE17 Km5004 |
| (5) | *Brevibacterium flavum* MJ-233 Km5005 | pPROBE17 Km5005 |
| (6) | *Brevibacterium flavum* MJ-233 Km5006 | pPROBE17 Km5006 |
| (7) | *Brevibacterium flavum* MJ-233 Km5007 | pPROBE17 Km5007 |
| (8) | *Brevibacterium flavum* MJ-233 Km5008 | pPROBE17 Km5008 |
| (9) | *Brevibacterium flavum* MJ-233 Km5009 | pPROBE17 Km5009 |
| (10) | *Brevibacterium flavum* MJ-233 Km5010 | pPROBE17 Km5010 |
| (11) | *Brevibacterium flavum* MJ-233 Km5011 | pPROBE17 Km5011 |
| (12) | *Brevibacterium flavum* MJ-233 Km5012 | pPROBE17 Km5012 |

Plasmid DNA was extracted from each of the twelve kanamycin resistant strains by a known method (Nucleic Acids Research, 9, 2898, (1981)).

The extracted plasmid DNA was again introduced into *Brevibacterium flavum* strain MJ-233 (FERM BP-1497) cells. The transformants were plated on A-medium agar plates containing 500 g/ml (final concentration) of kanamycin and incubated at 33° C. for 3 days. As a result, the transformants containing the plasmid DNA from any one of the twelve strains grew on the plates containing 500 µg/ml of kanamycin. Thus, it was confirmed that the kanamycin resistance of the transformants depended on the coryneform bacteria chromosomal DNA fragments inserted into the plasmid pPROBE17, and that the inserted DNA fragments were promoter DNA fragments which had greater promoter strengths than the tac promoter in coryneform bacteria cells.

To identify the DNA fragment having a greater promoter strength than the tac promoter, the sizes and nucleotide sequences of the DNA fragments inserted into the plasmid pPROBE17 were determined as follows:

First, the following primer two DNA fragments were chemically synthesized corresponding to nucleotide sequences of the plasmid pPROBE17 present in the upstream and downstream from the EcoRV site, that is, in the 5' and 3'-flanking sequences of the EcoRV site.

| Primer DNA for the 5' end: | GATCAGATCCCAGAATTGAT | (SEQ ID No. 19) |
| Primer DNA for the 3' end: | TGAGCGGGCTTTTTTTTGAT | (SEQ ID No. 20) |

Using these synthetic primer DNA sequences, plasmid DNA extracted from each of the twelve transformants was locally amplified by the PCR method (Nature, 324, 163 (1986), PCR condition; 9° C., 1 min.; 37° C., 2 min.; 72° C., 3 min.) using a DNA Thermal Cycler model 480 (Takara Shuzo Co., Ltd.). Thus, the DNA fragment inserted into the plasmid was selectively multiplied many times (i.e., amplified).

The insert DNA fragment thus amplified was electrophoresed on an agarose gel, followed by determining the sizes thereof based on the migration distances thereof on the agarose-gel with reference to the migration distance-size standard curve obtained by the electrophoresis of the pHY marker (Takara Shuzo Co., Ltd.) on the same agarose gel.

The nucleotide sequences of the amplified insert DNA fragment were determined by the dideoxy chain termination method (Proceedings of the National Academy of Science of the United States of America, 74, 5463 (1977)) using the same primers as used in the PCR method and the products of the PCR method as templates.

The results are shown below.

| No. | Plasmid | Size of insert DNA fragment | Sequence of insert DNA fragment |
|---|---|---|---|
| (1) | pPROBE17 | Km5001 about 130 bp | SEQ ID No: 1 |
| (2) | pPROBE17 | Km5002 about 410 bp | SEQ ID No: 2 |
| (3) | pPROBE17 | Km5003 about 420 bp | SEQ ID No: 3 |
| (4) | pPROBE17 | Km5004 about 240 bp | SEQ ID No: 4 |
| (5) | pPROBE17 | Km5005 about 600 bp | SEQ ID No: 5 |
| (6) | pPROBE17 | Km5006 about 590 bp | SEQ ID No: 6 |
| (7) | pPROBE17 | Km5007 about 430 bp | SEQ ID No: 7 |
| (8) | pPROBE17 | Km5008 about 860 bp | SEQ ID No: 8 |
| (9) | pPROBE17 | Km5009 about 1190 bp | SEQ ID No: 9 |
| (10) | pPROBE17 | Km5010 about 710 bp | SEQ ID No: 10 |
| (11) | pPROBE17 | Km5011 about 1000 bp | SEQ ID No: 11 |
| (12) | pPROBE17 | Km5012 about 740 bp | SEQ ID No: 12 |

Example 6

Detection of Controllable Promoter DNA Fragment in Coryneform Bacteria Chromosomal DNA 20 µg of the coryneform bacteria chromosomal DNA prepared in Example 4 was completely digested by incubation with the 4-base-sequence recognizing restriction enzymes AluI and HaeIII at 37° C. for 10 hours. Separately, 10 µg of the plasmid pPROBE17 DNA prepared in Example 2 was digested by incubation with the restriction enzyme EcoRV at 37° C. for one hour. After these resultant solutions were incubated at 65° C. for 10 minutes, they were mixed and then incubated at 16° C. for 24 hours in the presence of the T4 DNA ligase, ATP and dithiothreitol to ligate the DNA fragments. The ligation products were introduced into Brevibacterium flavum strain MJ-233 (FERMBP-1497) by the method described in Example 2. The transformants were selected by plating the resultant bacterial cells on a minimal medium obtained by adding 5 mg/liter of chloramphenicol and 20 g/liter of glucose to BT medium (prepared by dissolving 2 g of urea, 7 g of (NH4)2SO4, 0.5 g of K2HPO4, 0.5 g of KH2PO4, 0.5 g of MgSO4, 6 mg of FeSO4 7H2O, 6 mg of MnSO4 4–6H2O, 200 g of biotin, 200 µg of thiamine hydrochloride and 16 g of agar into distilled water to obtain 1 liter) and then incubating at 33° C. for 3 days. As a result, 100,000 of chloramphenicol resistant colonies were obtained.

Various methods for detecting different types of controllable promoter DNA fragments are described below.

Example 7

Detection of Controllable Promoter DNA Fragment Inducible by Replacing Glucose with Ethanol in the Medium Transformants isolated in Example 6 were replica-plated on a BT medium containing 20 g/liter of glucose and 100 µg/l of kanamycin (hereinafter, referred to as "GK medium") and a BT medium containing 20 ml/l of ethanol and 100 µg/l of kanamycin (hereinafter, referred to as "ET medium"), and then incubated at 33° C. for 3 days. As a result, four transformants which were unable to grow on GK medium but able to grow on EK medium were obtained. These transformants were named as follows:

| No. | Bacteria strain | Plasmid |
|---|---|---|
| (13) | Brevibacterium flavum MJ-233 KE101 | pPROBE17 KE101 |
| (14) | Brevibacterium flavum MJ-233 KE102 | pPROBE17 KE102 |
| (15) | Brevibacterium flavum MJ-233 KE103 | pPROBE17 KE103 |
| (16) | Brevibacterium flavum MJ-233 KE104 | pPROBE17 KE104 |

To determine whether the ability of the transformants to grow on a kanamycin-containing medium was caused by the promoter inserted into the plasmid pPROBE17, plasmid DNA was extracted from each of the four transformants and introduced again into coryneform bacteria cells, followed by examining the growth of the thus-obtained transformants on GK medium and EK medium in the same manner as described above. As a result, the transformants containing the plasmid DNA from any one of the four transformants were able to grow on EK medium but not on GK medium, thus confirming that the kanamycin resistance of the transformants substantially depended on the promoter DNA fragment inserted into the plasmid pPROBE17.

Next, to identify the thus-obtained promoters, the sizes and nucleotide sequences of the DNA fragments inserted into the plasmid pPROBE17 were determined by the methods described in Example 5. The results are shown below.

| No. | Bacteria strain | Plasmid |
|---|---|---|
| (13) | Brevibacterium flavum MJ-233 KE101 | pPROBE17 KE101 |
| (14) | Brevibacterium flavum MJ-233 KE102 | pPROBE17 KE102 |

Example 8

Detection of Controllable Promoter DNA Fragment Inducible by Replacing Ethanol with Glucose in the Medium Similar to Example 7, transformants isolated in Example 6 were replica-plated on GK medium and EK medium and incubated at 33° C. for 3 days. As a result, one transformant which was able to grow on GK medium but unable to grow on EK medium was obtained. The transformant and the plasmid contained therein were named *Brevibacterium flavum* MJ-233 KG101 and pPROBE17 KG101, respectively.

To determine whether the ability of the transformant to grow on a kanamycin-containing medium was caused by the promoter inserted into the plasmid pPROBE17, plasmid DNA was extracted from the transformant KG101 and introduced into other coryneform bacteria cells, followed by examining the growth of the thus-obtained transformants on GK medium and EK medium in the same manner as described above. As a result, the transformants containing the plasmid DNA from the transformant KG101 were able to grow on GK medium but not on EK medium, thus confirming that the kanamycin resistance of the transformant substantially depended on the promoter DNA fragment inserted into the plasmid pPROBE17.

Next, to identify the thus-obtained promoter, the size and nucleotide sequence of the DNA fragment inserted into the plasmid pPROBE17 KG101 were determined by the methods described in Example 5. The size of the DNA fragment was about 5,500 bp and the nucleotide sequence is listed as SEQ ID No. 15.

Example 9

Detection of Controllable Promoter DNA Fragment Inducible by Replacing with Fructose in the Medium Transformants isolated in Example 6 were replica-plated on GK medium and a BT medium containing 20 g/l of fructose and 100 μg/l of kanamycin (hereinafter, referred to as "FK medium) and incubated at 33° C. for 3 days. As a result, one transformant which was unable to grow on GK medium but able to grow on FK medium was obtained. The transformant and the plasmid contained therein were named *Brevibacterium flavum* MJ-233 KF101 and pPROBE17 KF101, respectively.

To determine whether the ability of the transformant to grow on a kanamycin-containing medium was caused by the promoter inserted into the plasmid pPROBE17, plasmid DNA was extracted from the transformant KF101 and introduced into other coryneform bacteria cells, followed by examining the growth of the thus-obtained transformants on GK medium and FK medium in the same manner as described above. As a result, the transformants containing the plasmid DNA from the transformant KF101 were able to grow on FK medium but not on GK medium, thus confirming that the kanamycin resistance of the transformant substantially depended on the promoter DNA fragment inserted into the plasmid pPROBE17.

Figure 5:
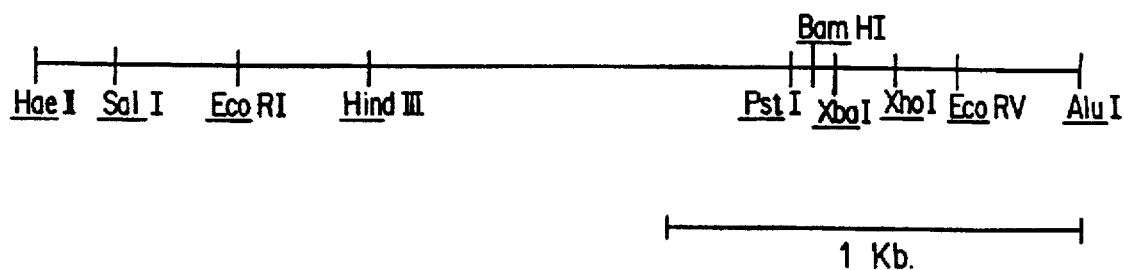
FIG. 5 shows a restriction map of a promoter DNA fragment whose promoter function is controllable by replacing the glucose with fructose in the culture medium for the host cell.

Next, to identify the thus-obtained promoter, the size of the DNA fragment inserted into the plasmid pPROBE17 KF101 was determined by the method described in Example 5. The size of the DNA fragment was about 2,500 bp. Further, the DNA fragment was digested with various restriction enzymes, and the sizes of the corresponding restriction fragments and the recognition sites were determined by agarose-gel electrophoresis. The results are shown in Table 2. The restriction map of the DNA fragment is shown in FIG. 5.

Example 10

Detection of Controllable Promoter DNA Fragment Inducible by Replacing Combination of Casein Hydrolysates, Yeast Extracts and Glucose with Glucose in the Medium Transformants isolated in Example 6 were replica-plated on GK medium and a BT medium containing 20 g/l of glucose, 1 g/l of yeast extracts, 1 g/l of casein hydrolysates (casamino acids) and 100 μg/ml of kanamycin (hereinafter, referred to as "GYCK medium) and incubated at 33° C. for 3 days. As a result, one transformant which was able to grow on GK medium but unable to grow on GYCK medium was obtained. The transformant and the plasmid contained therein were named *Brevibacterium flavum* MJ-233 KG102 and pPROBE17 KG102, respectively.

To determine whether the ability of the transformant to grow on a kanamycin-containing medium was caused by the promoter inserted into the plasmid pPROBE17, plasmid DNA was extracted from the transformant KG102 and introduced into other coryneform bacteria cells, followed by examining the growth of the thus-obtained transformants on GK medium and GYCK medium in the same manner as described above. As a result, the transformants containing the plasmid from the transformant KF101 were able to grow on GK medium but not on GYCK medium, thus confirming that the kanamycin resistance of the transformant substantially depended on the promoter DNA fragment inserted into the plasmid pPROBE17.

Next, to identify the thus-obtained promoter, the size and nucleotide sequence of the DNA fragment inserted into the plasmid pPROBE17 KG102 were determined by the methods described in Example 5. The size of the DNA fragment was about 5,700 bp and the nucleotide sequence is listed as SEQ ID No. 16.

Example 11

Detection of Controllable Promoter DNA Fragment Inducible by Replacing Glucose with Combination of Casein Hydrolysates, Yeast Extracts and Glucose in the Medium Similar to Example 10, transformants isolated in Example 6 were replica-plated on GK medium and GYCK medium and incubated at 33° C. for 3 days. As a result, three transformants which were unable to grow on GK medium but able to grow on GYCK medium were obtained. The transformants and the plasmid contained therein were named as follows:

| No. | Bacteria strain | Plasmid |
| --- | --- | --- |
| (20) | *Brevibacterium flavum* MJ-233 KGYC101 | pPROBE17 KGYC101 |
| (21) | *Brevibacterium flavum* MJ-233 KGYC102 | pPROBE17 KGYC102 |
| (22) | *Brevibacterium flavum* MJ-233 KGYC103 | pPROBE17 KGYC103 |

To determine whether the ability of the transformants to grow on a kanamycin-containing medium was caused by the promoter inserted into the plasmid pPROBE17, plasmid DNA was extracted from each of the three transformants and introduced into other coryneform bacteria cells, followed by examining the growth of the thus-obtained transformants on GK medium and GYCK medium in the same manner as described above. As a result, the transformants containing the plasmid from any one of the three transformants were able to grow on GYCK medium but not on GK medium, thus confirming that the kanamycin resistance of the transformants substantially depended on the promoter DNA fragment inserted into the plasmid pPROBE17.

Next, to identify the thus-obtained promoters, the sizes of the corresponding restriction fragments or nucleotide sequence of the DNA fragment inserted into the plasmid pPROBE17 KGYC101, pPROBE17 KGYC102 and pPROBE17 KGYC103 respectively were determined by the methods described herein above. The results are shown below.

| No. | Plasmid | Size of insert DNA fragment | Sequence of insert DNA fragment |
|---|---|---|---|
| (20) | pPROBE17 KGYC101 | about 1,110 bp | SEQ ID No: 17 |
| (21) | pPROBE17 KGYC102 | about 2,200 bp | Table 3 (FIG. 6) |
| (22) | pPROBE17 KGYC103 | about 2,300 bp | Table 4 (FIG. 7) |

What is claimed is:

1. An isolated DNA fragment which is obtained from coryneform bacteria chromosomal DNA and which is functional as a promoter in coryneform bacteria cells, wherein said DNA fragment has a greater promoter strength in coryneform bacteria cells than does a tac promoter in coryneform bacteria cells.

2. The isolated DNA fragment as claimed in claim 1, wherein said coryneform bacteria chromosomal DNA is chromosomal DNA obtained from *Brevibacterium flavum* MJ-233 (FERM BP-1497).

3. An isolated DNA fragment which is obtained from coryneform bacteria chromosomal DNA and which is functional as a promoter in coryneform bacteria cells and has greater promoter strength in coryneform bacteria cells than does a tac promoter in coryneform bacteria cells, wherein said promoter DNA fragment includes at least one of nucleotide sequences SEQ ID NOS. 1 to 12:

| SEQ ID NO. 1: | | | | | | | |
|---|---|---|---|---|---|---|---|
| GATCCATGCA | CGCGCGTTGC | TCGGGCTGAA | GGCCTGCTTC | CACCTCAGCG | GTGTGTTCAC | 60 |
| GGCGATCAAT | TTCTTTACCA | CCGAACACAT | ATCCATCACT | GGCCCATACT | CACCCCGACC | 120 |
| TGTAGGAT | | | | | | 128 |
| SEQ ID NO. 2: | | | | | | |
| GATCCACGCT | GAGCATTTGA | AAGTAACTAG | TCCCGAAGAT | CTTCGGAAAT | GCATAAAGCA | 60 |
| AAAGGCTCTT | AGTGGTTTGT | CAGCGTATGA | TCATCACGTA | GAGTAACACC | CAAGAGTAAG | 120 |
| ACGCAACATC | AATCAATGTG | CAAGGGTTTC | ATTTCTGGAA | ATCGTGGTCA | CCCCACATTC | 180 |
| ACCAGTAATG | AACAAGCTTG | TTTAATGTGA | ATTTGGAGTA | GACCACATGC | CCACTCTCGG | 240 |
| ACCATGGGAA | ATTGGAATCA | TTGTCCTGCT | GATCATCGTG | CTGTTCGGCG | CGAAGAAGCT | 300 |
| GCCTGATGCA | GCTCGTTCCA | TCGGCCAGAT | AACCCGCAGA | TCAAGACATC | AAACATTCGC | 360 |
| ACCATCGGAT | TTCTCATCTA | CGACGGCGTC | TCACCCCTCG | ATTTCACTGG | ATC | 413 |
| SEQ ID NO. 3: | | | | | | |
| GATCCCTGCC | CAGGCGCGCG | CCCGTCCTGG | CGAGTTCGCA | GATCGAAGGG | TTTGAACACC | 60 |
| GTAGAGGGTG | GCGTCGACAA | GCAAATTTCT | GGTTTGCTGC | AAGCCTTGCC | CTGTACTGGT | 120 |
| GCGCCGCGCT | GTGGATCGCG | CTGGACGTTG | GGTATTTCTG | GGGCGACGCG | CTCTCGCGCA | 180 |
| CCCAAGGCGC | CCTATCCGCG | CTGTACTCGC | GCAACCCCAC | GTTGTCGGCG | ATCGGTTACG | 240 |
| TGTTTACCCC | TCTGACCACC | GTGGTGCAGA | TTCCATTGGT | GGCGCTGAGC | CCCTGGGTCC | 300 |
| CGGAATTCAC | GCGCGCCGGG | TTGGCAGGCG | CATTGGTGTC | ATCAGTGTTC | ATGGCGGCTT | 360 |
| CAGTGAGGCA | ATTGTGGTTG | ATTGCCAGCG | AGCGCAACAT | CCGGTATTGG | CTCGCGGTGG | 420 |
| TAG | | | | | | 423 |
| SEQ ID NO. 4: | | | | | | |
| GATCTTTCAG | CTGCTCACAC | GTGATTGTAC | CGCGTCAATG | GAAGTGATTG | GCCGCTTCCT | 60 |
| TGCCTTGCTG | GAATTGTATA | AGGCACGCGC | TATTGAAACC | TTGCAAGAGG | AGCCACTCGG | 120 |
| CGAGCTTAAA | GTTTCGTGGA | CTGGCATTGA | TGTCGATCCA | GCAGTCGTCG | CGGCGAGTGA | 180 |
| CTGGGAGTAA | TCAGTTTTTC | TTAAGGAAAC | GTTGCTGAAT | TAGTTTTAGT | GACCTAAGAT | 240 |
| C | | | | | | 241 |
| SEQ ID NO. 5: | | | | | | |
| GATCTTGTCG | ACGCCGCCCG | CGACAGTGGC | GCACAAATCC | TCACGGGCGG | CCAACCCTCA | 60 |
| GATGGACCTG | GAAACTTCTA | TCCGGCCACG | ATTGTTACAG | ACATTGCTCC | GGATAATCCT | 120 |
| CTGGTTGTTG | AAGAACAGTT | CGGACCAGCG | CTTCCAATAG | TCCGATACTC | CAATATTGAT | 180 |
| GAAGCCATTG | GTTGGGCAAA | TGGACTTGAA | GTAGGTCTTG | GAGCTTCTGT | GTGGTCCGCT | 240 |

-continued

| | | | | | | |
|---|---|---|---|---|---|---|
| GATCGGAATC | GCGCAATGGA | TGTAGCTAGG | CAGATTCAGG | CTGGAACAGT | ATGGATTAAT | 300 |
| AACCATGCCC | GCCCTGATCC | AAGAATTCCT | TTCGGCGGAA | TCAAGCAATC | GGGATACGGC | 360 |
| CTTGAATTTG | GTGCTGATGG | CCTCAAAGCG | GTTGCGGTCC | CCAAGGTCTA | CAACGGTTAA | 420 |
| TTGTTTGATG | TTGAGAATTC | TCCGGGCCGA | TTATTGTCGT | AGTTTTCTGC | ATTGGTGCTT | 480 |
| GGCAAGGAGA | TCTGCCCCTG | GTAAAGCTTG | ATCAAATCGC | ATTTGACCAG | GGGATTTGGT | 540 |
| GTATTGTTAA | CTTGAAGGTA | GAGTATATTC | TCGTTCCTAA | AGGGGCCTAT | AGATC | 595 |

SEQ ID NO. 6:

| | | | | | | |
|---|---|---|---|---|---|---|
| GATCTGAAGC | AACACCTGAT | CAACCACACC | CCTTGGGGCG | CAAAGATCAC | GGTGGAGATC | 60 |
| GATGACATTA | ACCAACCGTT | CTCCACCGAT | ATTACCGGCC | CTGCAATGTC | CACCCTGGCG | 120 |
| TCCTGCCTGA | GCGCTGCGTA | CGAGGGCAAG | GATCTTGTCA | CCGAAGGCAG | CGGCGGATCC | 180 |
| ATTCCACTGT | GCACCGAACT | GATTGAGGTC | AACCCAGAAG | CAGAATTGGC | ACTCTACGGT | 240 |
| GTGGAAGAAC | CCCTCACCGT | TATCCACTCC | GCTAATGAAT | CTGTTGACCC | CAATGAGATT | 300 |
| CGCGATATCG | CCACCGCAGA | AGCATTGTTC | CTGCTCAACT | ACACCAAGTA | GACTTAGAAG | 360 |
| CAGGCATTAA | CACTGCCACC | TTTGCAAAAT | TAACCACCCC | CTGATGGGGT | GGTTTTTTCA | 420 |
| TGAGTTGAAA | AAAGTGTCTT | GATTCACTTT | GTGATGACGG | TTACCATAGC | CATCGTGACT | 480 |
| AAAAACATTG | ACCTTAAGCG | AGTAGCCAAG | GCTACGTACC | CTACTGCGGG | ATAGATGGAC | 540 |
| TGGCTCCCCG | CACTAGGGAA | GTAGTCGTTA | ATCAACACCA | AGAAGATC | | 588 |

SEQ ID NO. 7:

| | | | | | | |
|---|---|---|---|---|---|---|
| GATCTCAACG | TTTAGCGGCT | CTCTGGATCG | TGAAATGTCA | ACGTTCATGG | AAGCCAATGT | 60 |
| AGTGGGGTCG | CGTCGAAAAG | CGCGCTTTAA | GGGCGACACG | CCCAAAAAGT | TTTACCTTTA | 120 |
| AAAACTACCC | GCACGACCA | CGAACCTGTT | CAGTGATGCA | AATCACCGCT | AAAATATTGT | 180 |
| GGACGTTACC | CCCGCCTACC | GCTACGATTT | CAAAACATGA | CCATTTCCTC | ACCTTTGATT | 240 |
| GACGTCGCCA | ACCTTCCAGA | CATCAACACC | ACTGCCGGCA | AGATCGCCGA | CTTTAAGGCT | 300 |
| CGCCGCGCGG | AAGCCCATTT | CCCCATGGGT | GAAAAGGCAG | TAGAGAAGGT | CCACGCTGCT | 360 |
| GGACGCCTCA | CTGCCCGTGA | GCGCTTGGAT | TACTTACTCG | ATGAGGGCTC | TTCATCGAG | 420 |
| ACCGATCAGA | TC | | | | | 432 |

SEQ ID NO. 8:

| | | | | | | |
|---|---|---|---|---|---|---|
| CCGTTATATA | TAAGGAATAG | GCAACAAGTC | CCACTGGCTG | TGCCAATAGC | CAGCACACAA | 60 |
| ACATTGAATC | CCCACAGATC | ATCACCCAAA | ACTACGGGGC | TTGCAGTTCC | AATGCGATCA | 120 |
| AACCCATGGA | CAACATTGCC | ATGCGGATGC | TTCAGTTTTG | AATGAGGAGA | GCGGTAGATT | 180 |
| AGCCAACCGT | CAATTAATGA | CAATTGCCAC | CACAACAGCT | AACGCGAAGA | AGAAATCTGC | 240 |
| GACGACTGGA | AAACCATGGA | TTTTCAACAG | TGATGACAAC | AATGAGATGC | CCATGAGGGA | 300 |
| ACCAGCCCAC | GAGGGGCCCC | TTTGTGACAT | CGGCGTAGTT | GTTCAACTAT | AATGGAACGC | 360 |
| TGATCGTGGA | CAAGAGTTAA | CCATGAGATT | GATTCACCCC | TTTAAGCCTC | CAAAGAAGTA | 420 |
| GTTGACTCAA | CGCATTTCGG | CATTTAAAAA | AGCCGAGAGC | AAATGAGACT | TTCCAGGAGA | 480 |
| AGGCACCAGG | GACATGAACA | ATTGATCGGC | TGACCAACTC | TATAAGAGAT | GCACCTCAAG | 540 |
| TTTGGGGATA | CTTATTCGGC | GTTTCTGGGG | ACAAATACGT | TCCCTATTGT | TGTATATAGG | 600 |
| TATTCGCACT | TAAGAAACAT | CTCTCATGGA | AAGAAGCTAG | GCGGAAAGGG | CGTTAAGTAC | 660 |
| TTGCCATTTA | ATCCTCAGCA | TCACTCGGAT | CAGTCGGAGA | TGTCGATGAA | AATGCACCAG | 720 |
| GAGCCGTGGA | GAGCAGCATG | GTAGAAAACA | ACGTAGCAAA | AAAGACGGTC | GCTAAAAAGA | 780 |
| CCGCACGCAA | GACCGCACGC | AAAAGCAGCCC | CGCGCGTGGC | AACCCCATTG | GGAGTCGCAT | 840 |
| CTGAGTCTCC | CATTTCGG | | | | | 858 |

SEQ ID NO. 9:

| | | | | | | |
|---|---|---|---|---|---|---|
| TTACCGCAAG | CTCAATACGA | CTCACTATAG | GGGCCCGGTA | CCGAGCTCAC | TAGTTTAATT | 60 |
| AAAAGCTTAT | CGGCCTGAGG | TGAGAAGGGT | TCCGGACCCC | AGAATTCTCG | CGATAATTAA | 120 |
| TTAATAGCCC | GCCGTAATGA | GCGGGCTTTT | TTTTGATCCC | CGCCACCATA | ACCCACGAAT | 180 |
| CCTAACAAGT | CCCTGCATTC | TCGATGGCTT | TTTGGCTTTA | ATCCGTTTTG | GTTCAGGAAA | 240 |
| CTTACAAGAT | CTTTTACGCT | AGATGAAACT | TGCCATCGAA | CAGAATCCTG | CAGATGAAAT | 300 |
| CTTTCAGCAC | CATACATATC | GGTAATTCAT | AAAAATGCTCC | AGTGTCAAGC | TCTCGCAACG | 360 |
| TAATCGTTGC | TGTTCACGGA | GTTCTTACTA | GCTGCTCGGG | CGATCAATTT | GTCATTAGAT | 420 |
| TATGCAGTTA | TAGGGAGAAC | GGACACAAAA | GGGAGGGACC | TGACTGTACA | CTGTACTCCC | 480 |
| GCTAGCACGT | GTGTGTGATG | ACACAGCTCA | GAAGCATTGC | AGTTGGACAA | CCCCTAGATA | 540 |
| AGACTGCGCA | AAGTAGGACA | TATCTCTCAC | TTTTCTTATT | GTTTTCGGGC | AAAACTAATC | 600 |
| CAGAACCTTT | CTAAAGGCCC | TGATCAATCA | GGATTTCTGC | GTGTCGACGT | GATGCCACAC | 660 |
| CTGCTTGGGC | AAGCACCTTC | TGCAGGCGAA | CTCCGTCAGA | GTCATTGCGG | CTTAAGAAAC | 720 |
| CCATGACCA | ATCGTCGTCG | GATTTTACGT | TTTGCTTCTT | GGCAGCCTTA | GCGTTGGACA | 780 |
| GAAGAATCTC | ATCCTTCTTC | TGAGGCTGCT | GGCGTGTGTT | TGGGCGGGAT | GATCCTGGCT | 840 |
| TGTAGCCACG | AACTGAAGAC | CGGTATCCGC | CAGAGCGATT | GCTCTGCTTC | TTGTCCGGTG | 900 |
| TGCCATCTCG | GCGAGCGGGT | GGGGTCACGT | AAGTGTCCTT | AATCTTGAGA | GAAAACGTAT | 960 |
| GAAATTGAAT | CCCGTGAATT | CTAGCCTATT | TTAGGAGAATT | TTAATAGTCG | GGGCTTTAAC | 1020 |
| TGATGCTTTA | GAAGTCTTCA | TCAATGGAGT | CAACATCCGG | CAAAAGCGGT | GCTAGATCCG | 1080 |
| GTAATTTATC | CAAAGAATCA | ATACCCAACA | GCTCAAGCAG | GCAATTCCCG | TTGTGCCCAT | 1140 |
| AGCGGTGCGC | GCCCGTTGAT | TCGTCCACAT | CGACTTCTTT | GACTAGG | | 1187 |

SEQ ID NO. 10:

| | | | | | | |
|---|---|---|---|---|---|---|
| CTCAATTGCC | TCGTCTGAAG | GATGCTGACA | CTGAACTGAC | AGACGAGGAC | CGGGCCTAAG | 60 |
| ATTTTTTCGG | TGTATGGCGC | GGGCTGTGAG | GGGGATGTCG | TCGATAAGCG | TAGGGCCGAA | 120 |
| GAAGAAGCCC | TCCTCGTGCC | GTCTACGGCT | GCACGTTACG | CCGTCCACGA | CTGATCTTGG | 180 |
| CAGCCGGTCT | GGCCTCAGCG | ATGCGACATA | AGAAGCGACC | TTCTCGCGGT | GGCTGCGGTG | 240 |
| ATTAGTGGGC | CCAGGTCCGC | TCAGCCTGCT | CGCGCCGGCA | CCGTTGCCGA | TGCGAAGGGT | 300 |
| GTCGATGCGG | TCCTTGATCT | TCTCAATGAG | CTTTATTCCT | GGGCTTTGGG | AGCTTCAAAC | 360 |
| AGGAAGGCATC | AAATTTGGGG | TAGTGCAGGA | CCTTTGAATC | CCACCTCACA | GATAGTATTC | 420 |
| AGGCATTTCC | TTGTCACGAT | GGTTTATCCT | TGGACACAAC | ATCAAAAGTG | GGGTACATCA | 480 |
| TATGCTTCCG | GTTGAAAGTG | ACCTATCTGA | AAAGACTTGG | CAGAACCTTA | AGCAATGGTG | 540 |
| TGAACTGCGT | TAACGAATTT | TGTCGGACGT | TAAAATGGCG | CATTCTGCTT | GCTGAAGTGG | 600 |
| CACACCTATG | TGTTCTGCTT | GGGATAGCAG | TGCGGGAAAA | ATTTGAAAAA | GTCCGATTAC | 660 |

-continued

| | | | | | | |
|---|---|---|---|---|---|---|
| CTTGAGGAGT | ATTCAATGTC | ATGACGCATT | GCTTCAGAAA | ACTGCGCTCC | AAG | 713 |

SEQ ID NO. 11:

| | | | | | | |
|---|---|---|---|---|---|---|
| CTGAAGGAGT | ACACCTTCGA | TCTGCTCTAC | AGATCTTTAG | TGATAACAGA | AACTCAGTAC | 60 |
| TCCGAAGATC | TCTACTGACA | GATCTTGGAT | GGACCCGAGG | ATGTTAAAGC | GATTCCCTTC | 120 |
| GCTACAACAG | CAACAAGGCC | CTCAACAACC | TTGGCTACGA | AGGACTCTTC | CCAGCGGATG | 180 |
| AAACCAAGGT | GTCCCCAAAC | ATCTTGTCTG | CGCTGTCACC | AAACGCTGAT | GAGAACCACG | 240 |
| ACTTCTTCTC | CGGCTCCGGT | TCCTCTTACG | TTATTGGTAA | GGCAGAAAAC | ACCCGAGGAT | 300 |
| GATGACCTGG | GACTTTCTAA | CTTTTAAAAA | GCTGAAGCGG | TCTACCGCC | TGTAGGGTAA | 360 |
| CCTCAACCCG | TTAGAGCGTT | TTCGGGTTTC | CTGGTGGGA | CTTAAAGGTG | CGGGGTTTTC | 420 |
| CGAAGCCGCA | ATATCAGGGG | TAAGGGACGA | CCAGGCACCC | CTGTGGCCCC | TCGGCAGCGC | 480 |
| ATCACGCTTT | AGGAGAAAAC | GCCCCTGGAA | TGGCGTCTCA | ACCATTCAGA | TTGAACCCCG | 540 |
| GCAGGGGGA | ATTATGAAAT | CTGTGACAGG | GGTTAACCGT | GGGGGTGGGC | TTCCTGGCAG | 600 |
| AAATGTCCGT | CAAATTGTGA | ACCCCTTCAC | ACCTTTGGTT | GAAAGCACTG | CCCACAAGTG | 660 |
| ACTGAACCTG | GCAGCGACCT | CATGAATTGT | TTGAAAAACA | TTTTTTTGG | CACGAAAACG | 720 |
| GGGATACACG | TTAGCTGCAT | ACCAGCCTTT | TTGGGTTGCA | TCAGGATCCT | GCCTGTGGCC | 780 |
| TTATGATCAG | GCAGTGTTGT | TAAAGGACGA | TCGGTAATCC | GAATGGTTCG | TCCCGTAGTC | 840 |
| AGGAGGAACC | TATGACCGCT | GTGGCGCCTA | GGGTCGACGG | GCACGTGCCC | CTCTACGAGG | 900 |
| CCCGAGCCCG | ACAGGCCATG | CACGCAAGGG | CAGAAAGCAT | GGTTAATGAT | GACCACCACC | 960 |
| GGACCACAAG | CAGCTTGGGC | ATTATGTACA | TCATTATGTC | CTTCAG | | 1006 |

SEQ ID NO. 12:

| | | | | | | |
|---|---|---|---|---|---|---|
| CTGCGTTGGC | CTTAAGGGAG | ATCACTTCAA | TTTCTTCATT | GTGAGGCAGC | CAGAACTCCA | 60 |
| CCACCTTTTC | CTGCTCTGAA | AGTCCATCCA | CTGTGAAGCA | CCTGCGGATC | TTCCAGACGC | 120 |
| CGTTCCGTGG | CGCCGGTGAT | GAAATTGACT | TCCGTGGTCT | CGCCCCGGA | GGTTGGCGTG | 180 |
| GAAGATGTGG | GGGCGCCGTC | GATAAGCACA | TCAATCTTGC | CGCCCGGCCG | GCCGGAATCG | 240 |
| AGGTACACCA | CCGAGTGGAN | TACGTGGTCA | GCGTGAAGGA | GGTGGCGGTT | GGTGCGACAC | 300 |
| ACACCGCACG | CCCGTTGGTT | GGCGTTCCAT | CGCGCTAACT | TGGGATCACA | GTACGGTCTA | 360 |
| CTTATTCCTT | TGCTGAGCCA | ATCGGGCGAA | GGCCCCTTGT | TAGTGGTTCA | ATTTCGGTTG | 420 |
| CGCCGTGAAT | TAAATTCGGG | ATTTCATGAG | CTTAACCGTA | CCGCTCTTGC | AGAGTTCACA | 480 |
| GGGTAAACCC | TAAATGGAAC | AACCCATTGC | CAATATGTTG | GTTAAGTTGT | ACGCAAGTAA | 540 |
| ATCTTTTCAA | TCGTGGAAGC | AGGGCTCACA | GTCTAATGGC | ACGTATGCAG | GAAAGCGCCG | 600 |
| ATCTTCCAAA | TGTTCCTTCT | GCGGAAAGAG | CCAAAAGCAG | GTAAAAAAAC | TTCATCGCGG | 660 |
| GTGGCGCCGG | TATATATCTT | GTGATGAGTG | CATTGAGCTT | GTGCAACGAG | ATTATTGAAG | 720 |
| AAGAACTCAG | GTCAAGA | | | | | 737 |

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 128 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ233

( i x ) FEATURE:
        ( A ) NAME/KEY: promoter
        ( B ) LOCATION: 1-128
        ( C ) IDENTIFICATION METHOD: experiment ( x i ) SEQUENCE DESCRIPTION:SEQ ID NO:1:

```
GATCCATGCA  CGCGCGTTGC  TCGGGCTGAA  GGCCTGCTTC  CACCTCAGCG  GTGTGTTCAC   60
GGCGATCAAT  TTCTTTACCA  CCGAACACAT  ATCCATCACT  GGCCCATACT  CACCCCGACC  120
TGTAGGAT                                                                128
```

( 2 ) INFORMATION FOR SEQ ID NO:2:

( i ) SEQUENCE CHARACTERISTICS:
        ( A ) LENGTH: 413 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ233

( i x ) FEATURE:
        ( A ) NAME/KEY: promoter
        ( B ) LOCATION: 1-413
        ( C ) IDENTIFICATION METHOD: experiment ( x i ) SEQUENCE DESCRIPTION:SEQ ID NO:2:

```
GATCCACGCT  GAGCATTTGA  AAGTAACTAG  TCCCGAAGAT  CTTCGGAAAT  GCATAAAGCA   60
AAAGGCTCTT  AGTGGTTTGT  CAGCGTATGA  TCATCACGTA  GAGTAACACC  CAAGAGTAAG  120
ACGCAACATC  AATCAATGTG  CAAGGGTTTC  ATTTCTGGAA  ATCGTGGTCA  CCCCACATTC  180
```

| ACCAGTAATG | AACAAGCTTG | TTTAATGTGA | ATTTGGAGTA | GACCACATGC | CCACTCTCGG | 240 |
| ACCATGGGAA | ATTGGAATCA | TTGTCCTGCT | GATCATCGTG | CTGTTCGGCG | CGAAGAAGCT | 300 |
| GCCTGATGCA | GCTCGTTCCA | TCGGCCAGAT | AACCCGCAGA | TCAAGACATC | AAACATTCGC | 360 |
| ACCATCGGAT | TTCTCATCTA | CGACGGCGTC | TCACCCCTCG | ATTCACTGG | ATC | 413 |

( 2 ) INFORMATION FOR SEQ ID NO:3:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ233

( i x ) FEATURE:
        ( A ) NAME/KEY: promoter
        ( B ) LOCATION: 1-423
        ( C ) IDENTIFICATION METHOD: experiment ( x i ) SEQUENCE DESCRIPTION:SEQ ID NO:3:

| GATCCCTGCC | CAGGCGCGCG | CCCGTCCTGG | CGAGTTCGCA | GATCGAAGGG | TTTGAACACC | 60 |
| GTAGAGGGTG | GCGTCGACAA | GCAAATTTCT | GGTTTGCTGC | AAGCCTTGCC | CTGTACTGGT | 120 |
| GCGCCGCGCT | GTGGATCGCG | CTGGACGTTG | GGTATTTCTG | GGGCGACGCG | CTCTCGCGCA | 180 |
| CCCAAGGCGC | CCTATCCGCG | CTGTACTCGC | GCAACCCCAC | GTTGTCGGCG | ATCGGTTACG | 240 |
| TGTTTACCCC | TCTGACCACC | GTGGTGCAGA | TTCCATTGGT | GGCGCTGAGC | CCCTGGGTCC | 300 |
| CGGAATTCAC | GCGCGCCGGG | TTGGCAGGCG | CATTGGTGTC | ATCAGTGTTC | ATGGCGGCTT | 360 |
| CAGTGAGGCA | ATTGTGGTTG | ATTGCCAGCG | AGCGCAACAT | CCGGTATTGG | CTCGCGGTGG | 420 |
| TAG | | | | | | 423 |

( 2 ) INFORMATION FOR SEQ ID NO:4:

( i ) SEQUENCE CHARACTERISTICS:
        ( A ) LENGTH: 241 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ233

( i x ) FEATURE:
        ( A ) NAME/KEY: promoter
        ( B ) LOCATION: 1-241
        ( C ) IDENTIFICATION METHOD: experiment ( x i ) SEQUENCE DESCRIPTION:SEQ ID NO:4:

| GATCTTTCAG | CTGCTCACAC | GTGATTGTAC | CGCGTCAATG | GAAGTGATTG | GCCGCTTCCT | 60 |
| TGCCTTGCTG | GAATTGTATA | AGGCACGCGC | TATTGAAACC | TTGCAAGAGG | AGCCACTCGG | 120 |
| CGAGCTTAAA | GTTTCGTGGA | CTGGCATTGA | TGTCGATCCA | GCAGTCGTCG | CGGCGAGTGA | 180 |
| CTGGGAGTAA | TCAGTTTTTC | TTAAGGAAAC | GTTGCTGAAT | TAGTTTAGT | GACCTAAGAT | 240 |
| C | | | | | | 241 |

( 2 ) INFORMATION FOR SEQ ID NO:5:

( i ) SEQUENCE CHARACTERISTICS:
    ( A ) LENGTH: 595 base pairs
    ( B ) TYPE: nucleic acid
    ( C ) STRANDEDNESS: double
    ( D ) TOPOLOGY: linear ( i i ) MOLECULE TYPE: genomic DNA ( v i ) ORIGINAL SOURCE:
    ( A ) ORGANISM: Brevibacterium flavum
    ( B ) STRAIN: MJ233

( i x ) FEATURE:
    ( A ) NAME/KEY: promoter
    ( B ) LOCATION: 1-595
    ( C ) IDENTIFICATION METHOD: experiment ( x i ) SEQUENCE DESCRIPTION:SEQ ID NO:5:

```
GATCTTGTCG ACGCCGCCCG CGACAGTGGC GCACAAATCC TCACGGGCGG CCAACCCTCA   60
GATGGACCTG GAAACTTCTA TCCGGCCACG ATTGTTACAG ACATTGCTCC GGATAATCCT  120
CTGGTTGTTG AAGAACAGTT CGGACCAGCG CTTCCAATAG TCCGATACTC AATATTGAT   180
GAAGCCATTG GTTGGGCAAA TGGACTTGAA GTAGGTCTTG GAGCTTCTGT GTGGTCCGCT  240
GATCGGAATC GCGCAATGGA TGTAGCTAGG CAGATTCAGG CTGGAACAGT ATGGATTAAT  300
AACCATGCCC GCCCTGATCC AAGAATTCCT TTCGGCGGAA TCAAGCAATC GGGATACGGC  360
CTTGAATTTG GTGCTGATGG CCTCAAAGCG GTTGCGGTCC CCAAGGTCTA CAACGGTTAA  420
TTGTTTGATG TTGAGAATTC TCCGGGCCGA TTATTGTCGT AGTTTCTGC ATTGGTGCTT   480
GGCAAGGAGA TCTGCCCCTG GTAAAGCTTG ATCAAATCGC ATTTGACCAG GGGATTTGGT  540
GTATTGTTAA CTTGAAGGTA GAGTATATTC TCGTTCCTAA AGGGCCTAT AGATC        595
```

( 2 ) INFORMATION FOR SEQ ID NO:6:

( i ) SEQUENCE CHARACTERISTICS:
    ( A ) LENGTH: 588 base pairs
    ( B ) TYPE: nucleic acid
    ( C ) STRANDEDNESS: double
    ( D ) TOPOLOGY: linear ( i i ) MOLECULE TYPE: genomic DNA ( v i ) ORIGINAL SOURCE:
    ( A ) ORGANISM: Brevibacterium flavum
    ( B ) STRAIN: MJ233

( i x ) FEATURE:
    ( A ) NAME/KEY: promoter
    ( B ) LOCATION: 1-588
    ( C ) IDENTIFICATION METHOD: experiment ( x i ) SEQUENCE DESCRIPTION:SEQ ID NO:6:

```
GATCTGAAGC AACACCTGAT CAACCACACC CCTTGGGGCG CAAAGATCAC GGTGGAGATC   60
GATGACATTA ACCAACCGTT CTCCACCGAT ATTACCGGCC CTGCAATGTC CACCCTGGCG  120
TCCTGCCTGA GCGCTGCGTA CGAGGGCAAG GATCTTGTCA CCGAAGGCAG CGGCGGATCC  180
ATTCCACTGT GCACCGAACT GATTGAGGTC AACCCAGAAG CAGAATTGGC ACTCTACGGT  240
GTGGAAGAAC CCCTCACCGT TATCCACTCC GCTAATGAAT CTGTTGACCC CAATGAGATT  300
CGCGATATCG CCACCGCAGA AGCATTGTTC CTGCTCAACT ACACCAAGTA GACTTAGAAG  360
CAGGCATTAA CACTGCCACC TTTGCAAAAT TAACCACCCC CTGATGGGGT GGTTTTTTCA  420
TGAGTTGAAA AAAGTGTCTT GATTCACTTT GTGATGACGG TTACCATAGC CATCGTGACT  480
AAAAACATTG ACCTTAAGCG AGTAGCCAAG GCTACGTACC CTACTGCGGG ATAGATGGAC  540
```

```
TGGCTCCCCG CACTAGGGAA GTAGTCGTTA ATCAACACCA AGAAGATC            588
```

( 2 ) INFORMATION FOR SEQ ID NO:7:

( i ) SEQUENCE CHARACTERISTICS:
        ( A ) LENGTH: 432 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ233

( i x ) FEATURE:
        ( A ) NAME/KEY: promoter
        ( B ) LOCATION: 1-432
        ( C ) IDENTIFICATION METHOD: experiment ( x i ) SEQUENCE DESCRIPTION:SEQ ID NO:7:

```
GATCTCAACG TTTAGCGGCT CTCTGGATCG TGAAATGTCA ACGTTCATGG AAGCCAATGT    60
AGTGGGGTCG CGTCGAAAAG CGCGCTTTAA GGGCGACACG CCCAAAAAGT TTACCTTTA    120
AAAACTACCC GCACGCAGCA CGAACCTGTT CAGTGATGCA AATCACCGCT AAAATATTGT   180
GGACGTTACC CCCGCCTACC GCTACGATTT CAAAACATGA CCATTCCTC ACCTTTGATT    240
GACGTCGCCA ACCTTCCAGA CATCAACACC ACTGCCGGCA AGATCGCCGA CTTTAAGGCT   300
CGCCGCGCGG AAGCCCATTT CCCCATGGGT GAAAAGGCAG TAGAGAAGGT CCACGCTGCT   360
GGACGCCTCA CTGCCCGTGA GCGCTTGGAT TACTTACTCG ATGAGGGCTC CTTCATCGAG   420
ACCGATCAGA TC                                                      432
```

( 2 ) INFORMATION FOR SEQ ID NO:8:

( i ) SEQUENCE CHARACTERISTICS:
        ( A ) LENGTH: 858 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ233

( i x ) FEATURE:
        ( A ) NAME/KEY: promoter
        ( B ) LOCATION: 1-858
        ( C ) IDENTIFICATION METHOD: experiment ( x i ) SEQUENCE DESCRIPTION:SEQ ID NO:8:

```
CCGTTATATA TAAGGAATAG GCAACAAGTC CCACTGGCTG TGCCAATAGC CAGCACACAA    60
ACATTGAATC CCCACAGATC ATCACCCAAA ACTACGGGGC TTGCAGTTCC AATGCGATCA   120
AACCCATGGA CAACATTGCC ATGCGGATGC TTCAGTTTTG AATGAGGAGA GCGGTAGATT   180
AGCCAACCGT CAATTAATGA CAATTGCCAC CACAACAGCT AACGCGAAGA AGAAATCTGC   240
GACGACTGGA AAACCATGGA TTTTCAACAG TGATGACAAC AATGAGATGC CCATGAGGGA   300
ACCAGCCCAC GAGGGGCCCC TTTGTGACAT CGGCGTAGTT GTTCAACTAT AATGGAACGC   360
TGATCGTGGA CAAGAGTTAA CCATGAGATT GATTCACCCC TTTAAGCCTC CAAAGAAGTA   420
GTTGACTCAA CGCATTTCGG CATTTAAAAA AGCCGAGAGC AAATGAGACT TTCCAGGAGA   480
AGGCACCAGG GACATGAACA ATTGATCGGC TGACCAACTC TATAAGAGAT GCACCTCAAG   540
```

```
TTTGGGGATA   CTTATTCGGC   GTTTCTGGGG   ACAAATACGT   TCCCTATTGT   TGTATATAGG   600

TATTCGCACT   TAAGAAACAT   CTCTCATGGA   AAGAAGCTAG   GCGGAAAGGG   CGTTAAGTAC   660

TTGCCATTTA   ATCCTCAGCA   TCACTCGGAT   CAGTCGGAGA   TGTCGATGAA   AATGCACCAG   720

GAGCCGTGGA   GAGCAGCATG   GTAGAAAACA   ACGTAGCAAA   AAAGACGGTC   GCTAAAAGA    780

CCGCACGCAA   GACCGCACGC   AAAGCAGCCC   CGCGCGTGGC   AACCCCATTG   GGAGTCGCAT   840

CTGAGTCTCC   CATTTCGG                                                         858
```

(2) INFORMATION FOR SEQ ID NO:9:

(i) SEQUENCE CHARACTERISTICS:
        (A) LENGTH: 1187 base pairs
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Brevibacterium flavum
        (B) STRAIN: MJ233

(ix) FEATURE:
        (A) NAME/KEY: promoter
        (B) LOCATION: 1-1187
        (C) IDENTIFICATION METHOD: experiment (xi) SEQUENCE DESCRIPTION:SEQ ID NO:9:

```
TTACCGCAAG   CTCAATACGA   CTCACTATAG   GGGCCCGGTA   CCGAGCTCAC   TAGTTTAATT   60

AAAAGCTTAT   CGGCCTGAGG   TGAGAAGGGT   TCCGGACCCC   AGAATTCTCG   CGATAATTAA   120

TTAATAGCCC   GCCGTAATGA   GCGGGCTTTT   TTTGATCCC   CGCCACCATA   ACCCACGAAT    180

CCTAACAAGT   CCCTGCATTC   TCGATGGCTT   TTTGGCTTTA   ATCCGTTTTG   GTTCAGGAAA   240

CTTACAAGAT   CTTTTACGCT   AGATGAAACT   TGCCATCGAA   CAGAATCCTG   CAGATGAAAT   300

CTTTCAGCAC   CATACATATC   GGTAATTCAT   AAAATGCTCC   AGTGTCAAGC   TCTCGCAACG   360

TAATCGTTGC   TGTTCACGGA   GTTCTTACTA   GCTGCTCGGG   CGATCAATTT   GTCATTAGAT   420

TATGCAGTTA   TAGGGAGAAC   GGACACAAAA   GGGAGGGACC   TGACTGTACA   CTGTACTCCC   480

GCTAGCACGT   GTGTGTGATG   ACACAGCTCA   GAAGCATTGC   AGTTGGACAA   CCCCTAGATA   540

AGACTGCGCA   AAGTAGGACA   TATCTCTCAC   TTTTCTTATT   GTTTCGGGC   AAAACTAATC    600

CAGAACCTTT   CTAAAGGCCC   TGATCAATCA   GGATTCTGC   GTGTCGACGT   GATGCCACAC    660

CTGCTTGGGC   AAGCACCTTC   TGCAGGCGAA   CTCCGTCAGA   GTCATTGCGG   CTTAAGAAAC   720

CCATCGACCA   ATCGTCGTCG   GATTTTACGT   TTTGCTTCTT   GGCAGGCTTA   GCGTTGGAGA   780

GAAGAATCTC   ATCCTTCTTC   TGAGGCTGCT   GGCGTGTGTT   TGGGCGGGAT   GATCCTGGCT   840

TGTAGCCACG   AACTGAAGAC   CGGTATCCGC   CAGAGCGATT   GCTCTGCTTC   TTGTCCGGTG   900

TGCCATCTCG   GCGAGCGGGT   GGGGTCACGT   AAGTGTCCTT   AATCTTGAGA   GAAAACGTAT   960

GAAATTGAAT   CCCGTGAATT   CTAGCCTATT   TTAGGAGATT   TAATAGTCG   GGGCTTTAAC    1020

TGATGCTTTA   GAAGTCTTCA   TCAATGGAGT   CAACATCCGG   CAAAAGCGGT   GCTAGATCCG   1080

GTAATTTATC   CAAAGAATCA   ATACCCAACA   GCTCAAGCAG   GCAATTCCCG   TTGTGCCCAT   1140

AGCGGTGCGC   GCCCGTTGAT   TCGTCCACAT   CGACTTCTTT   GACTAGG                   1187
```

(2) INFORMATION FOR SEQ ID NO:10:

(i) SEQUENCE CHARACTERISTICS:
        (A) LENGTH: 713 base pairs
        (B) TYPE: nucleic acid (C) STRANDEDNESS: double
(D) TOPOLOGY: linear (i i) MOLECULE TYPE: genomic DNA (v i) ORIGINAL SOURCE:
    (A) ORGANISM: Brevibacterium flavum
    (B) STRAIN: MJ233

(i x) FEATURE:
    (A) NAME/KEY: promoter
    (B) LOCATION: 1-713
    (C) IDENTIFICATION METHOD: experiment (x i) SEQUENCE DESCRIPTION:SEQ ID NO:10:

```
CTCAATTGCC TCGTCTGAAG GATGCTGACA CTGAACTGAC AGACGAGGAC CGGGCCTAAG    60
ATTTTTTCGG TGTATGGCGC GGGCTGTGAG GGGGATGTCG TCGATAAGCG TAGGGCCGAA   120
GAAGAAGCCC TCCTCGTGCC GTCTACGGCT GCACGTTACG CCGTCCACGA CTGATCTTGG   180
CAGCCGGTCT GGCCTCAGCG ATGCGACATA AGAAGCGACC TTCTCGCGGT GGCTGCGGTG   240
ATTAGTGGGC CCAGGTCCGC TCAGCCTGCT CGCGCCGGCA CCGTTGCCGA TGCGAAGGGT   300
GTCGATGCGG TCCTTGATCT TCTCAATGAG CTTTATTCCT GGGCTTTGGG AGCTTCAAAC   360
AGGAGGCATC AAATTTGGGG TAGTGCAGGG CCTTTGAATC CCACCTCACA GATAGTATTC   420
AGGCATTTCC TTGTCACGAT GGTTTATCCT TGGACACAAC ATCAAAAGTG GGGTACATCA   480
TATGCTTCCG GTTGAAAGTG ACCTATCTGA AAGACTTGG CAGAACCTTA AGCAATGGTG   540
TGAACTGCGT TAACGAATTT TGTCGGACGT TAAAATGGCG CATTCTGCTT GCTGAAGTGG   600
CACACCTATG TGTTCTGCTT GGGATAGCAG TGCGGGAAAA ATTTGAAAAA GTCCGATTAC   660
CTTGAGGAGT ATTCAATGTC ATGACGCATT GCTTCAGAAA ACTGCGCTCC AAG          713
```

(2) INFORMATION FOR SEQ ID NO:11:

(i) SEQUENCE CHARACTERISTICS:
        (A) LENGTH: 1006 base pairs
        (B) TYPE: nucleic acid
        (C) STRANDEDNESS: double
        (D) TOPOLOGY: linear (i i) MOLECULE TYPE: genomic DNA (v i) ORIGINAL SOURCE:
        (A) ORGANISM: Brevibacterium flavum
        (B) STRAIN: MJ233

(i x) FEATURE:
        (A) NAME/KEY: promoter
        (B) LOCATION: 1-1006
        (C) IDENTIFICATION METHOD: experiment (x i) SEQUENCE DESCRIPTION:SEQ ID NO:11:

```
CTGAAGGAGT ACACCTTCGA TCTGCTCTAC AGATCTTTAG TGATAACAGA AACTCAGTAC    60
TCCGAAGATC TCTACTGACA GATCTTGGAT GGACCCGAGG ATGTTAAAGC GATTCCCTTC   120
GCTACAACAG CAACAAGGCC CTCAACAACC TTGGCTACGA AGGACTCTTC CCAGCGGATG   180
AAACCAAGGT GTCCCCAAAC ATCTTGTCTG CGCTGTCACC AAACGCTGAT GAGAACCACG   240
ACTTCTTCTC CGGCTCCGGT TCCTCTTACG TTATTGGTAA GGCAGAAAAC ACCCGAGGAT   300
GATGACCTGG GACTTTCTAA CTTTTAAAAA GCTGAAGCGG TCTACCGGCC TGTAGGGTAA   360
CCTCAACCCG TTAGAGCGTT TTCGGGTTTC CTGGTGGGGA CTTAAAGGTG CGGGGTTTTC   420
CGAAGCCGCA ATATCAGGGG TAAGGGACGA CCAGGCACCC CTGTGGCCCC TCGGCAGCGC   480
ATCACGCTTT AGGAGAAAAC GCCCCTGGAA TGGCGTCTCA ACCATTCAGA TTGAACCCCG   540
```

```
GCAGGGGGGA  ATTATGAAAT  CTGTGACAGG  GGTTAACCGT  GGGGGTGGGC  TTCCTGGCAG   600

AAATGTCCGT  CAAATTGTGA  ACCCCTTCAC  ACCTTTGGTT  GAAAGCACTG  CCCACAAGTG   660

ACTGAACCTG  GCAGCGACCT  CATGAATTGT  TTGAAAACA   TTTTTTTGG   CACGAAAACG   720

GGGATACACG  TTAGCTGCAT  ACCAGCCTTT  TTGGGTTGCA  TCAGGATCCT  GCCTGTGGCC   780

TTATGATCAG  GCAGTGTTGT  TAAAGGACGA  TCGGTAATCC  GAATGGTTCG  TCCCGTAGTC   840

AGGAGGAACC  TATGACCGCT  GTGGCGCCTA  GGGTCGACGG  GCACGTGCCC  CTCTACGAGG   900

CCCGAGCCCG  ACAGGCCATG  CACGCAAGGG  CAGAAAGCAT  GGTTAATGAT  GACCACCACC   960

GGACCACAAG  CAGCTTGGGC  ATTATGTACA  TCATTATGTC  CTTCAG                  1006
```

(2) INFORMATION FOR SEQ ID NO:12:

(i) SEQUENCE CHARACTERISTICS:
        (A) LENGTH: 737 base pairs
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Brevibacterium flavum
        (B) STRAIN: MJ233

(ix) FEATURE:
        (A) NAME/KEY: promoter
        (B) LOCATION: 1-737
        (C) IDENTIFICATION METHOD: experiment (xi) SEQUENCE DESCRIPTION:SEQ ID NO:12:

```
CTGCGTTGGC  CTTAAGGGAG  ATCACTTCAA  TTTCTTCATT  GTGAGGCAGC  CAGAACTCCA    60

CCACCTTTTC  CTGCTCTGAA  AGTCCATCCA  CTGTGAAGCA  CCTGCGGATC  TTCCAGACGC   120

CGTTCCGTGG  CGCCGGTGAT  GAAATTGACT  TCCGTGGTCT  CGCCCCCGGA  GGTTGGCGTG   180

GAAGATGTGG  GGGCGCCGTC  GATAAGCACA  TCAATCTTGC  CGCCCGGCCG  GCCGGAATCG   240

AGGTACACCA  CCGAGTGGAN  TACGTGGTCA  GCGTGAAGGA  GGTGGCGGTT  GGTGCGACAC   300

ACACGGCACG  CCCGTTGGTT  GGCGTTCCAT  CGCGCTAACT  TGGGATCACA  GTACGGTCTA   360

CTTATTCCTT  TGCTGAGCCA  ATCGGGCGAA  GGCCCCTTGT  TAGTGGTTCA  ATTTCGGTTG   420

CGCCGTGAAT  TAAATTCGGG  ATTTCATGAG  CTTAACCGTA  CCGCTCTTGC  AGAGTTCACA   480

GGGTAAACCC  TAAATGGAAC  AACCCATTGC  CAATATGTTG  GTTAAGTTGT  ACGCAAGTAA   540

ATCTTTTCAA  TCGTGGAAGC  AGGGCTCACA  GTCTAATGGC  ACGTATGCAG  GAAAGCGCCG   600

ATCTTCCAAA  TGTTCCTTCT  GCGGAAAGAG  CCAAAAGCAG  GTAAAAAAAC  TTCATCGCGG   660

GTGGCGCCGG  TATATATCTT  GTGATGAGTG  CATTGAGCTT  GTGCAACGAG  ATTATTGAAG   720

AAGAACTCAG  GTCAAGA                                                     737
```

(2) INFORMATION FOR SEQ ID NO:13:

(i) SEQUENCE CHARACTERISTICS:
        (A) LENGTH: 2203 base pairs
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Brevibacterium flavum
        (B) STRAIN: MJ233

(ix) FEATURE:

(A) NAME/KEY: promoter
(B) LOCATION: 1-2203
(C) IDENTIFICATION METHOD: experiment (xi) SEQUENCE DESCRIPTION:SEQ ID NO:13:

| | | | | | | |
|---|---|---|---|---|---|---|
| CTACTTCTTC | TTCACCGAAG | TATTCCTTAG | GGTCGATCTC | GTTACCCTCG | GAGTCCTTCA | 60 |
| CGTTTACGCG | GCAGATAGCC | TGTGCAAGAG | CCTTGCCACG | GCGAACGTCG | GAGAAGAGGT | 120 |
| TCGCGATCTG | GCCGGACTGC | TGCAGCTGAC | CGATGAACTG | GTTTGGGTCC | ATGCCGTAAG | 180 |
| ACTGTGCGGT | GAACAGGATG | TGGTCGGTGA | GCTCCTCGTG | CCGCTGATGC | GACTTCGAGT | 240 |
| CCGATCCAGC | CACCACCGAT | GAGGACCAGC | TTTTTACCTT | CACCGAAGTT | GCCTTGATCG | 300 |
| CGTCAGAGTC | TTCCACGGCG | CGCAGGTAGT | GCACATTAGA | GCCGTCGGCT | CCGGAATTGG | 360 |
| AAGTTTGCGA | CTGCTGAGCA | AGTAGCAAGA | ACTAGTTTGT | CGTAGTTAAT | GGTCTCAGTG | 420 |
| TTTCCGCCAT | CATCAACGGT | GACTTGGCGT | GAACCCGCAT | CAATTGCCGT | GACGCACACC | 480 |
| TTGACGCAGC | GTGACATTGT | TTTCTTTGTA | CCACCCCGCC | GGGTGAACAA | TCGCCTTTTC | 540 |
| AAAGCCTACT | TTTCCCGCCA | TGTACTCCTT | TGACAGCGGT | GGGCGTTCAT | ATGGCAGATG | 600 |
| ATTTTCTGCT | GCGATGAGCG | TGATGGAGCC | TTCATGCCCG | TTTACACGCA | GTGCCTCTGC | 660 |
| GGTTTTCGCT | CCGGCTGAAC | CGCCGCCGAT | GATGACGATG | CTTTGTGGTG | TGCTCATGCT | 720 |
| GTACTCCTAG | TCCCTAAAAA | GTGGACGGTC | AGGCGCAAGG | TCGACCGCAT | GGTCTATACG | 780 |
| CCATGCTAGT | TAAAAGGCCG | AAACCCTCGG | CGAGCGCGCT | AAATACCCGG | CCCCAATTGG | 840 |
| GGGTGTGAGG | CAGCACACAA | GACGAAACCC | TAACGAAATC | GCCAGACTCC | TCGCAATCAC | 900 |
| AAGAAGCGAC | GACTAGCCTG | TGGGACAAA | CTATCTCAAG | AATTTATTCA | ACAAAGGAGT | 960 |
| TCTTCGCACA | TGAAGGAAGT | AGCAGTCAAC | GAAGTCCCAG | CAGGCGCGCA | GCTAATGCAC | 1020 |
| TGTCACTGTT | TCGACGTGAT | GTGCATCGGT | TTACGTGGTG | GCGTGGTTCA | CACATTGCTC | 1080 |
| CATCGGGCAT | TGGTGCGTCA | ATCGGTTTGG | GTTTTAAGT | TTTGTGCGGG | GGTGGTCACC | 1140 |
| CCTGTTGTGA | ACTTTGCAAA | GTTATGACTT | CGCAGAAAAA | GTCGGCGGGG | GAGTTGCTAG | 1200 |
| TACGGATGTA | CTGGGCAAAT | GCTCTGAAAT | GGGAAAATGC | AGGCACCACA | ACTTTCCGTA | 1260 |
| GTTTGAAGG | TGTGACCTAG | ATAAAAGTCG | GGGTTAGGCG | GGGGTAAATG | ACTAGGTAAA | 1320 |
| GGTTCGCAAA | CCCCCTTTTG | TTGGTGACGG | TGATCACTTA | GTCTGATCAC | ATCGCCAAAC | 1380 |
| ACGATAAGGG | TTGAAATCGA | AAGAAGAGCG | GCACCTAGAT | TCCAGAGGTA | GCCAGAGTGC | 1440 |
| TTTTCTTAAA | AGAGTTTTCA | CAACCGTTAA | CGGCGTAGCC | AAACAAGAAG | GATTCGCATT | 1500 |
| NCAGCTTCTG | GTTAGGCAC | AGGTCATCTA | AAACCCATGC | TTTAAAAGGA | GCCTTCAATG | 1560 |
| ACTGAACAGG | AACTGTTGTC | TGCTCAGACT | GCCGACAACG | CTGGAACTGA | CAGCACCGAA | 1620 |
| CGCGTTGACG | CGGGCGGAAT | GCAGGTTGCA | AAAGTTCTCT | ACGACTTTGT | AACCGAAGCG | 1680 |
| GTACTCCCTC | GCGTGGGTGT | GGATGCGGAA | AAGTTCTGGT | CCGGATTCGC | CGCCATCGCC | 1740 |
| CGGGACCTCA | CCCCACGCAA | CCGCGAACTG | CTTGCTCGTC | GCGATGAACT | GCAGACGCTT | 1800 |
| ATCGACGACT | ACCACCGCAA | CAACTCCGGC | ACCATCGACC | AAGACGCGTA | CGAGGATTTC | 1860 |
| CTTAAAGAAA | TCGGATACTT | GGTTGAGGAG | CCAGAAGCTG | CAGAAATCCG | TACCCAAAAC | 1920 |
| GTCGATACGG | AAATCTCCAG | CACCGCAGAC | CTCAGCTGGT | TGTGCCAATT | CTGAACGCAC | 1980 |
| GTTCGCGCTG | AATGCTGCCA | ATGCTCGTTG | GGGTTCCCTC | TACGATGCGT | TGTACGGCAC | 2040 |
| CAACGCCATC | CCAGAAACTG | ATGGCGCTGA | AAAGGGCAAG | GAGTACAACC | CGGTCCGCGG | 2100 |
| CCAGAAGGTC | ATCGAGTCGG | GTCGTCAATT | CCTCGACAGC | GTTGTCCAC | TGGACGGGTG | 2160 |
| CTTCGCATGC | CGATGTTGAG | AAGTACAACA | TCACGGATGG | AAA | | 2203 |

( 2 ) INFORMATION FOR SEQ ID NO:14:

( i ) SEQUENCE CHARACTERISTICS:
        ( A ) LENGTH: 551 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ233

( i x ) FEATURE:
        ( A ) NAME/KEY: promoter
        ( B ) LOCATION: 1-551
        ( C ) IDENTIFICATION METHOD: experiment ( x i ) SEQUENCE DESCRIPTION:SEQ ID NO:14:

```
CCTCATGGAT GTTGACATCG ATATGGATTC CGACATCTGA GCAGATCCTC TCCTGGCGGA    60
CACAGACGCA TCCCTGCTCT CCCTGGAAGC TGGCACCTGT GACCGTTGCC TTCGACACGA   120
CACATGCTGA CCACCCTGGA GAACTCCGGC CTATCGTGCC GATCGTTCCA GGCGCTGTGA   180
TTTTTGATTT GTTGGTGGGC GATCCCAAAA ACAGGCCGCT GAGAAAGTTT TCCACACTAA   240
AATAGTGTGA TTCTGCCGAA TCTGTTGTTT TACTTTTGAA ACTGCGGGAT CATGAAAAGT   300
AGTGAAAAGT GAATTTTAGT TCTGTGCTTT CTCTTCCCTT TAAGTGAACC TTTTGTTGGA   360
TCTTCATTAA AAAAATGAAA ACCTCGTCGG AATGCAACTT GGGATCACTG TCTCGGGCAA   420
GAAACGGCCT TAAAAAGGG GAGTGATTGT GAGTGCTTGA TTTCTTAGCT GCGAACCCGC    480
TTGATTGCTG CTTGGTGGTT ATTTGGCCA CGGGTGACCA CTCCCAGACT CAGCTGCCAG    540
GTGGTCAGTG G                                                        551
```

( 2 ) INFORMATION FOR SEQ ID NO:15:

( i ) SEQUENCE CHARACTERISTICS:
        ( A ) LENGTH: 549 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ233

( i x ) FEATURE:
        ( A ) NAME/KEY: promoter
        ( B ) LOCATION: 1-549
        ( C ) IDENTIFICATION METHOD: experiment ( x i ) SEQUENCE DESCRIPTION:SEQ ID NO:15:

```
GATCCTCATG GATGTTGACA TCGATATGGA TTCCGACATC GAGCAGATCC TCTCCGGCGG    60
ACACGACGCA TCCCTGCTCT CCCTGGAAGC TGGCACCTGT GACGTTGCCT TCGCACACGA   120
CACCATGCTG ACCACCCTGG AGAACTCCGG CCTATCGTGC CGATCGTTCC AGGCGCTGTG   180
ATTTTTGATT TGTTGGTGGG CGATCCCAAA AACAGGCCGC TGAGAAAGTT TTCCACACTA   240
AAATAGTGTG ATTCTGTCCG AATCTGTTGT TTTAGTTTTG AAACTGCGGG ATCATGGAAA   300
GTAGTGAAAA GTGAATTTTA GTTCTGTGCT TTCTCTGCCC TTTAAGTGAA CCTTTTGTTG   360
GATCTTGCAT TAAAAAAATG AAAACCTCGT CGGGAATGCA ACTTGGGATC ACGTCTGGG    420
CAAGAAACGT CCTTAAAAAA GGGGAGTGAT TGTGAGTGCT TGATTTCTTA GCTGCGAACC   480
```

```
CGCTGATTGC GCTGGTGGTT ATTTTGGCCA CGGTGACCAC TCCCGACTCG GCGCCGGTGG  540

TCGTGGATC                                                          549
```

( 2 ) INFORMATION FOR SEQ ID NO:16:

( i ) SEQUENCE CHARACTERISTICS:
        ( A ) LENGTH: 567 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ233

( i x ) FEATURE:
        ( A ) NAME/KEY: promoter
        ( B ) LOCATION: 1-567
        ( C ) IDENTIFICATION METHOD: experiment ( x i ) SEQUENCE DESCRIPTION:SEQ ID NO:16:

```
GATCCAAAAA GTCGGCGCAG CTGACTGGAG CTTCTGGGAA GCCAAAGTCC GCGCCCGCGA   60

CTACGCCCTG GACGAAACCG AACTGCGCAA CTACTTCCCA CTGAACCAAG TACTCTGTGA  120

CGGCGTCTTC TTCGCTGCTA ACCGCCTCTA CGGAATCACC GTGGAACCAC GCCCTGACCT  180

GCGCGGTTAC GCCGAGGGCG TGGACGTCTG GGAAGTCCTC GATTCTGACG GCTCCGGCAT  240

CGGCCACAAG TGCGATGCGC CCCTTCCGGG TCGGCGAGGC GGTGATCTTG CGGTGTCTAC  300

CTGGGGTCGA CTGTCGAGTC GTGGTCCGCA TTGAACTTCT TTCCGTGGTG TTTATCTTTT  360

CATCACAAAC AATCACGACG GTATACCCAT CGGAGACGAT ATCGTGATCT TTCTGTTACC  420

TGCGGAAGGT AACATTAGTA TTTCAACTCG ACAGAGTCCA TCCTGGAAGC GTGTATGACG  480

ATTTCTTCAC ACATTCTTTA CAATGGCCTT TCGTGCGATA ATGCTAGGCA TGCTTCGATG  540

GACTACAGCA GGTGAATCCC ACGGATC                                     567
```

( 2 ) INFORMATION FOR SEQ ID NO:17:

( i ) SEQUENCE CHARACTERISTICS:
        ( A ) LENGTH: 1107 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ233

( i x ) FEATURE:
        ( A ) NAME/KEY: promoter
        ( B ) LOCATION: 1-1107
        ( C ) IDENTIFICATION METHOD: experiment ( x i ) SEQUENCE DESCRIPTION:SEQ ID NO:17:

```
CTGGTTTTGG CGGTAGGCAA ACATGCCTTT GAGGGTAGAT GCCGGTAGGC GGAGTGCTCA   60

CGGAATCTGT GATGAGTGTG CCGCCGTCTT GGTCGATGAA ATTGTGCACG TGACGCCAGT  120

TTGCGAGGGC CTTTACGGGG GCGGTCAGAC AGACGTCGGT GAAGCGTGAA CCATTCAAAA  180

ATCCCGATAA ATCATGGCGC GCCACCCATT TAAGTCCCGC AGGAAGGCTG AAAATGGTGG  240

TGCCATCGGA GAGGCGTTCT GCCTGCGCAA TGGGGTTAAG GGGGACGAAT GGCGGAGTCA  300

GACGTGTGAC AGCGCCCTTA CGGGTATGCC AATCCCAGAC CATTTCTCGG GGAAAAGGAA  360
```

```
TAAAATGGCT  TGTGGTCAGA  CTCACAGGGG  CTTCTCCAAG  TCAGTGGATT  TATGAGGTCC   420

CAGTGGGTAC  ACACCGGGTG  TCCTACAACG  ATCAATTGTC  ACAGATTCGA  CTGGCATGCT   480

GTACCATCTG  CTTTAAGCAT  TTTGGTGTTT  CACTGTTGTT  AACAGTGTTT  CACCGTGGAG   540

CACTACCTAA  AGATCATAGT  CAGCATCTTG  GGGTGAATGT  GACACGGTAC  GCTATAGTGT   600

CAGACAACAA  CCAGGAAACT  GGTCGTTGCA  GAGTTTTGC   AAAATTGGAC  ATCCTTTAAC   660

GGACCGCACA  GAGAGGCGGG  AAGGAGGTCA  CGATGAGCGA  ACGTAATAGT  GCTGTACTAG   720

AACTCCTCAA  TGAGGACGAC  GTCAGCCGTA  CCATCGCACG  CATCGCGCAC  CAGATTATTG   780

AGAAAACCGC  GCTTGATTCC  AAATACGCGG  ATCGGGTCAT  GTTGTTAGGC  ATTCCTTCAG   840

GTGGAGTCCC  GCTGGCCCGA  AGGCTTGCTG  AAAAGATCGA  AGAATTTCC   GGCGTTTCGG   900

TAGATACCGG  CGCTGTTGAT  ATCACCTTGT  ACAGGGATGA  TCTTCGAAAC  AAACCGCACC   960

GCGCACTGCA  GCCCACCTCT  ATTCCGGCAG  GTGGTATCGA  TAACACCACC  GTGATTTTGG  1020

TGGATGATGT  GCTGTTTTCC  GGTCGTACTA  TNCGCGCTGC  ACTTGATGCA  TTGCGCGACG  1080

TTGGACGCCC  AAACTATATC  CAATTAG                                         1107
```

( 2 ) INFORMATION FOR SEQ ID NO:18:

( i ) SEQUENCE CHARACTERISTICS:
        ( A ) LENGTH: 61 base pairs
        ( B ) TYPE: nucleic acid
        ( C ) STRANDEDNESS: double
        ( D ) TOPOLOGY: linear ( i i ) MOLECULE TYPE: Other nucleic acid
        ( A ) DESCRIPTION: Synthetic ( i i i ) HYPOTHETICAL: NO ( i v ) ANTI-SENSE: NO ( x i ) SEQUENCE DESCRIPTION: SEQ ID NO:18:

```
AATTCTCGCG  ATAATTAATT  AATAGCCCGC  CTAATGAGCG  GGCTTTTTTT  TGATATCAAT    60
T                                                                         61
```

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: Other nucleic acid
        ( A ) DESCRIPTION: Synthetic ( i i i ) HYPOTHETICAL: NO ( i v ) ANTI-SENSE: NO ( x i ) SEQUENCE DESCRIPTION: SEQ ID NO:19:

```
GATCAGATCC  CAGAATTGAT                                                    20
```

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: Other nucleic acid
        ( A ) DESCRIPTION: Synthetic ( i i i ) HYPOTHETICAL: NO ( i v ) ANTI-SENSE: NO ( x i ) SEQUENCE DESCRIPTION: SEQ ID NO:20:

TGAGCGGGCT TTTTTTTGAT                                                    20

( 2 ) INFORMATION FOR SEQ ID NO:21:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: Other nucleic acid
        ( A ) DESCRIPTION: Synthetic ( i i i ) HYPOTHETICAL: NO ( i v ) ANTI-SENSE: NO ( x i ) SEQUENCE DESCRIPTION: SEQ ID NO:21:

GATCTCAAGA AGATCCTTTG ATCTTTCTA CGGATCCCAG                               40